US008906896B2

(12) United States Patent
Bierbach

(10) Patent No.: US 8,906,896 B2
(45) Date of Patent: Dec. 9, 2014

(54) PLATINUM ACRIDINE ANTI-CANCER COMPOUNDS AND METHODS THEREOF

(76) Inventor: Ulrich Bierbach, Winston-Salem, NC (US)

( * ) Notice: Subject to any disclaimer, the term of this patent is extended or adjusted under 35 U.S.C. 154(b) by 894 days.

(21) Appl. No.: 13/125,214

(22) PCT Filed: Oct. 23, 2009

(86) PCT No.: PCT/US2009/061832
§ 371 (c)(1),
(2), (4) Date: Jun. 30, 2011

(87) PCT Pub. No.: WO2010/048499
PCT Pub. Date: Apr. 29, 2010

(65) Prior Publication Data
US 2012/0039800 A1    Feb. 16, 2012

Related U.S. Application Data

(60) Provisional application No. 61/108,317, filed on Oct. 24, 2008, provisional application No. 61/178,836, filed on May 15, 2009.

(51) Int. Cl.
*A61K 31/555* (2006.01)
*C07F 15/00* (2006.01)
*A61K 45/06* (2006.01)
*A61K 31/47* (2006.01)
*A61K 31/55* (2006.01)

(52) U.S. Cl.
CPC .............. *C07F 15/0093* (2013.01); *A61K 45/06* (2013.01); *A61K 31/47* (2013.01); *A61K 31/55* (2013.01)
USPC ........................................... 514/185; 546/10

(58) Field of Classification Search
USPC ........................................... 514/185; 546/10
See application file for complete search history.

(56) References Cited

U.S. PATENT DOCUMENTS

| 4,843,161 | A | 6/1989 | Lippard et al. |
| 6,313,333 | B1 | 11/2001 | Da Re et al. |
| 2006/0035963 | A1 | 2/2006 | Ashwell et al. |

OTHER PUBLICATIONS

Ma, Z. et al.: A non-cross-linking Platinum-acridine agent with potent activity in Non-small-cell lung cancer. J.Med. Chem., vol. 51, pp. 7574-7580, 2008.*
Kelland, L., The resurgence of platinum-based cancer chemotherapy. Nat. Rev. Cancer 2007, 7, 573-584.
Rabik, C. A.; Dolan, M. E., Molecular mechanisms of resistance and toxicity associated with platinating agents. Cancer Treat. Rev. 2007, 33, 9-23.
Cosaert, J.; Quoix, E., Platinum drugs in the treatment of non-small-cell lung cancer. Br. J. Cancer 2002, 87, 825-833.

Wakelee, H.; Dubey, S.; Gandara, D., Optimal adjuvant therapy for non-small cell lung cancer—how to handle stage I disease. Oncologist 2007, 12, 331-337.
Soria, J. C.; Le Chevalier, T., Is cisplatin still the best platinum compound in non-small-cell lung cancer? Ann. Oncol. 2002, 13, 1515-1517.
Momekov, G.; Bakalova, A.; Karaivanova, M., Novel approaches towards development of non-classical platinum-based antineoplastic agents: design of platinum complexes characterized by an alternative DNA-binding pattern and/or tumor-targeted cytotoxicity. Curr. Med. Chem. 2005, 12, 2177-2191.
Guddneppanavar, R.; Bierbach, U., Adenine-n3 in the DNA minor groove—an emerging target for platinum containing anticancer pharmacophores. Anticancer Agents Med. Chem. 2007, 7, 125-138.
Martins, E. T.; Baruah, H.; Kramarczyk, J.; Saluta, G.; Day, C. S.; Kucera, G. L.; Bierbach, U., Design, synthesis, and biological activity of a novel non-cisplatin-type platinum-acridine pharmacophore. J. Med. Chem. 2001, 44, 4492-4496.
Baruah, H.; Rector, C. L.; Monnier, S. M.; Bierbach, U., Mechanism of action of non-cisplatin type DNA-targeted platinum anticancer agents: DNA interactions of novel acridinylthioureas and their platinum conjugates. Biochem. Pharmacol. 2002, 64, 191-200.
Barry, C. G.; Baruah, H.; Bierbach, U., Unprecedented monofunctional metalation of adenine nucleobase in guanine-and thymine-containing dinucleotide sequences by a cytotoxic platinum-acridine hybrid agent. J. Am. Chem. Soc. 2003, 125, 9629-9637.
Barry, C. G.; Day, C. S. Bierbach, U., Duplex-promoted platination of adenine-N3 in the minor groove of DNA: challenging a longstanding bioinorganic paradigm. J. Am. Chem. Soc. 2005, 127, 1160-1169.
Baruah, H.; Wright, M. W.; Bierbach, U., Solution structural study of a DNA duplex containing the guanine-N7 adduct formed by a cytotoxic platinum-acridine hybrid agent. Biochemistry 2005, 44, 6059-6070.
Budiman, M. E.; Alexander, R. W.; Bierbach, U., Unique base-step recognition by a platinum-acridinylthiourea conjugate leads to a DNA damage profile complementary to that of the anticancer drug cisplatin. Biochemistry 2004, 43, 8560-8567.
Connors, T. A.; Cleare, M. J.; Harrap, K. R., Structure-Activity-Relationships of the Anti-Tumor Platinum Coordination-Complexes. Cancer Treat. Rep. 1979, 63, 1499-1502.
Hess, S. M.; Mounce, A. M.; Sequeira, R. C.; Augustus, T. M.; Ackley, M. C.; Bierbach, U., Platinum-acridinylthiourea conjugates show cell line-specific cytotoxic enhancement in H460 lung carcinoma cells compared to cisplatin. Cancer Chemother. Pharmacol. 2005, 56, 337-343.

(Continued)

*Primary Examiner* — Charanjit Aulakh
(74) *Attorney, Agent, or Firm* — Ben Schroeder Law

(57) ABSTRACT

Acridine containing cisplatin compounds are disclosed that show greater efficacy than other cisplatin compounds for treating cancer. The compounds are compounds of Formula I Formula I wherein the variables are defined herein.

25 Claims, 5 Drawing Sheets

(56) References Cited

OTHER PUBLICATIONS

Guddneppanavar, R.; Choudhury, J. R.; Kheradi, A. R.; Steen, B. D.; Saluta, G.; Kucera, G. L.; Day, C. S.; Bierbach, U., Effect of the diamine nonleaving group in platinum-acridinylthiourea conjugates on DNA damage and cytotoxicity. J. Med. Chem. 2007, 50, 2259-2263.

Guddneppanavar, R.; Saluta, G.; Kucera, G. L.; Bierbach, U., Synthesis, biological activity, and DNA-damage profile of platinum-threading intercalator conjugates designed to target adenine. J. Med. Chem. 2006, 49, 3204-3214.

Kukushkin, V. Y.; Pombeiro, A. J., Additions to metal-activated organonitriles. Chem. Rev. 2002, 102, 1771-1802.

Ackley, M. C.; Barry, C. G.; Mounce, A. M.; Farmer, M. C.; Springer, B. E.; Day, C. S.; Wright, M. W.; Berners-Price, S. J.; Hess, S. M.; Bierbach, U., Structure-activity relationships in platinum-acridinylthiourea conjugates: effect of the thiourea nonleaving group on drug stability, nucleobase affinity, and in vitro cytotoxicity. J. Biol. Inorg. Chem. 2004, 9, 453-461.

Guddneppanavar, R.; Wright, M. W.; Tomsey, A. K.; Bierbach, U., Guanine binding of a cytotoxic platinum-acridin-9-ylthiourea conjugate monitored by 1-D 1H and 2-D [1H-15N] NMR spectroscopy: Hydrolysis is not the rate-determining step. J. Inorg. Biochem. 2006, 100, 972-979.

Gelasco, A.; Lippard, S. J., Anticancer activity of cisplatin and related complexes. In: Topics in Biological Inorganic Chemistry, vol. 1; Clarke, M. J., Sadler, P. J., Eds.; Springer: New York, 1999, pp. 1-43.

Baruah, H.; Day, C. S.; Wright, M. W.; Bierbach, U., Metal-intercalator-mediated self-association and one-dimensional aggregation in the structure of the excised major DNA adduct of a platinum-acridine agent. J. Am. Chem. Soc. 2004, 126, 4492-4493.

Margiotta, N.; Habtemariam, A.; Sadler, P. J., Strong, rapid binding of a platinum complex to thymine and uracil under physiological conditions. Angew Chem Int. Ed. Engl. 1997, 36, 1185-1187.

Manzotti, C.; Pratesi, G.; Menta, E.; Di Domenico, R.; Cavalletti, E.; Fiebig, H. H.; Kelland, L. R.; Farrell, N.; Polizzi, D.; Supino, R.; Pezzoni, G.; Zunino, F., BBR 3464: A novel triplatinum complex, exhibiting a preclinical profile of antitumor efficacy different from cisplatin. Clin. Cancer Res. 2000, 6, 2626-2634.

Hollis, L. S.; Amundsen, A. R.; Stern, E. W., Chemical and Biological Properties of a New Series of Cis-Diammineplatinum(II) Antitumor Agents Containing 3 Nitrogen Donors—Cis-[Pt(NH3)2(N-Donor)Cl]+. J. Med. Chem. 1989, 32, 128-136.

Lovejoy, K. S.; Todd, R. C.; Zhang, S.; McCormick, M. S.; D'Aquino, J. A.; Reardon, J. T.; Sancar, A.; Giacomini, K. M.; Lippard, S. J., cis-Diammine(pyridine)chloroplatinum(II), a monofunctional platinum(II) antitumor agent: Uptake, structure, function, and prospects. Proc. Natl. Acad. Sci. USA 2008, 105, 8902-8907.

Gray, J.; Simon, G.; Bepler, G., Molecular predictors of chemotherapy response in non-small-cell lung cancer. Expert Rev. Anticancer Ther. 2007, 7, 545-549.

Weaver, D. A.; Crawford, E. L; Warner, K. A.; Elkhairi, F.; Khuder, S. A.; Willey, J. C., ABCC5, ERCC2, XPA and XRCC1 transcript abundance levels correlate with cisplatin chemoresistance in non-small cell lung cancer cell lines. Mol. Cancer 2005, 4, 18.

Fujii, T.; Toyooka, S.; Ichimura, K.; Fujiwara, Y.; Hotta, K.; Soh, J.; Suehisa, H.; Kobayashi, N.; Aoe, M.; Yoshino, T.; Kiura, K.; Date, H., ERCC1 protein expression predicts the response of cisplatin-based neoadjuvant chemotherapy in non-small-cell lung cancer. Lung Cancer 2008, 59, 377-384.

Soria, J. C., ERCC1-tailored chemotherapy in lung cancer: the first prospective randomized trial. J. Clin. Oncol. 2007, 25, 2648-2649.

Zamble, D. B.; Mu, D.; Reardon, J. T.; Sancar, A.; Lippard, S. J., Repair of cisplatin—DNA adducts by the mammalian excision nuclease. Biochemistry 1996, 35, 10004-10013.

Dip, R.; Camenisch, U.; Naegeli, H., Mechanisms of DNA damage recognition and strand discrimination in human nucleotide excision repair. DNA Repair 2004, 3, 1409-1423.

Poklar, N.; Pilch, D. S.; Lippard, S. J.; Redding, E. A.; Dunham, S. U.; Breslauer, K. J., Influence of cisplatin intrastrand crosslinking on the conformation, thermal stability, and energetics of a 20-mer DNA duplex. Proc. Natl. Acad. Sci. USA 1996, 93, 7606-7611.

Ma, Zhidong, Jayati Roy Choudhury, Marcus W. Wright, Cynthia S. Day, Gilda Saluta, Gregory L. Kucera, and Ulrich Bierbach, A Non-Cross-Linking Platinum-Acridine Agent with Potent Activity in Non-Small-Cell Lung Cancer, J. Med. Chem. 2008, 51, 7574-7580.

Ma, Zhidong, Cynthia S. Day, and Ulrich Bierbach, Unexpected Reactivity of the 9-Aminoacridine Chromophore in Guanidylation Reactions, J. Org. Chem. 2007, 72, 5387-5390.

International Search Report for PCT/US09/61832 sent Dec. 23, 2009 and references cited therein.

Alderden, The Distribution of Platinum Complexes in Biological Systems, Ph. D. Thesis, Feb. 2006.

Canadian Office Action for Application No. 2741683 sent Jan. 21, 2013.

Canadian Office Action for Application No. 2741683 sent Dec. 13, 2013.

Response to Canadian Office Action for Application No. 2741683 of Jan. 21, 2013 filed Jul. 18, 2013.

Response to Canadian Office Action for Application No. 2741683 of Dec. 13, 2013 filed Jun. 10, 2014.

Translation of Japanese Office Action for Application No. JP 2011-533365 sent Mar. 11, 2014.

Supplementary European Search Report for EP 09 82 2767 sent May 9, 2012 and references cited therein.

Kheradi A R et al., Bioorganic & Medicinal Chem Lett., 19(13), 2009, pp. 3423-3425.

Reply to European Patent Application No. 09822767.1 sent Mar. 11, 2013.

Bonivento, M.; Canovese, L.; Cattalini, L.; Marangoni, G.; Michelson, G.; Tobe, M. L. Cis effect of dimethylsulfide and leaving group effect in reactions of the cationic complex chloro(dimethyl sulfide)(1,2-diaminoethane)platinum(II) chloride. Inorg. Chem. 1981, 20, 3728-3730.

Bonivento, M.; Cattalini, L.; Marangoni, G.; Michelson, G.; Schwab, A. P.; Tobe, M. L. The cis effect of dimethyl sulfoxide in the reactions of the cationic complex chloro(dimethyl sulfoxide)(1,2-diaminoethane)platinum(II) chloride. Inorg. Chem. 1980, 19, 1743-1746.

Ma, Z. Structure-Activity Relationship Studies of Hybrid Antitumor Agents for the Treatment of Non-Small Cell Lung Cancer. Dissertation, Wake Forest University, 2009.

International Preliminary Report on Patentability for PCT/US09/61832 issued Apr. 26, 2011.

\* cited by examiner

PLATINUM ACRIDINE ANTI-CANCER COMPOUNDS AND METHODS THEREOF

This application claims priority under 35 USC §§119(e), 363 and 371 to U.S. Provisional Applications 61/108,317 filed Oct. 24, 2008 and 61/178,836 filed May 15, 2009, the entire contents of both are incorporated by reference in their entireties.

STATEMENT REGARDING FEDERALLY SPONSORED RESEARCH OR DEVELOPMENT

Some aspects of this invention described in this application were sponsored by R01 CA 101880 (NIH/NCI). Accordingly, the Federal Government has rights in this application.

FIELD OF THE INVENTION

The present invention relates to new platinum containing compounds that show increased potency and efficacy in vitro and in vivo against certain types of cancer.

BACKGROUND OF THE INVENTION

Cisplatin is an inorganic platinum agent (cis-diamminedichloroplatinum or cis-DDP) with anti-neoplastic activity, which forms highly reactive, charged, platinum complexes which bind to nucleophilic groups such as GC-rich sites in DNA, inducing intrastrand and interstrand DNA cross-links, as well as DNA-protein cross-links. These cross-links result in apoptosis and cell growth inhibition.

Formation of any platinated coordination complex with DNA is not sufficient for cytotoxic (that is, cell-killing) activity. The corresponding trans isomer of cisplatin (namely, trans-DDP) also forms a coordination complex with DNA but unlike cisplatin, trans-DDP is not an effective chemotherapeutic agent.

Cisplatin has been shown effective against lung cancer, testicular cancers, ovarian carcinomas, various head and neck cancers, and patients with lymphomas. However, better drugs are always desired that have greater potency and less toxicity. Moreover, there are certain types of cancer against which cisplatin is not effective.

Previously, health care workers have used cisplatin in combination therapies to treat cancer. However, despite the hope that the drugs will work together, producing a synergistic, or at least an additive effect, to cure the cancer has proved elusive. Moreover, not only has combination therapy with cisplatin failed to show additive effects, there often have been other deleterious side effects caused by the combination therapy. Even if the side effects present in combination therapy are minimized, the costs often times prove to be prohibitive.

Some combination therapies have proved to be somewhat effective against certain types of cancers. An example that has been used is the combination of cisplatin with 5-fluorouracil to treat terminally ill colon carcinoma patients. In one study, the tumors in three of nine patients decreased in size by more than 50% for varying lengths of time. However, cisplatin alone showed no effect on colon cancers in phase I clinical trials.

Resistance to platinum drugs, perhaps the most serious drawback, is multifactorial in nature, which complicates the design of compounds able to circumvent the underlying resistance mechanisms. While certain tumors tend to acquire resistance after treatment with platinum, other forms of the disease are inherently chemoresistant. Non-small cell lung cancer (NSCLC), for instance, a major cause of cancer-related mortality worldwide, is notoriously insensitive to treatment with classical cytotoxic agents, including the first generation of platinum-based drugs. Despite the poor clinical prognosis of the disease, dual-agent regimens containing cisplatin (or less toxic carboplatin) in combination with a non-platinum agent are currently the only treatment options for patients with advanced NSCLC. This sobering fact demonstrates the urgent need for novel chemotypes to combat this aggressive form of cancer.

Cellular Uptake of Cisplatin

Cisplatin generally is administered to cancer patients intravenously as a sterile sodium chloride saline solution. Once cisplatin is in the bloodstream, it is believed that cisplatin remains intact due the relatively high concentration of chloride ions (~100 mM). The neutral compound is thought to enter the cell either by passive diffusion or active uptake. Inside the cell, the neutral cisplatin molecule undergoes hydrolysis, in which a chlorine ligand is replaced by a molecule of water, generating a positively charged species. Hydrolysis occurs inside the cell because the concentration of chloride ion is much lower, in the range of ~3-20 mM.

The following reactions are the postulated mechanism for the process that occurs in the cell:

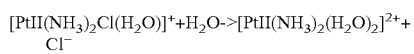

Cisplatin is thought to coordinate with DNA mainly through the N7 nitrogen on purine bases. Generally; these nitrogen atoms (specifically, the N7 atoms of purines) are free to coordinate to cisplatin because they do not form hydrogen bonds with any other DNA bases.

Many types of cisplatin-DNA coordination complexes, or adducts, can be formed. The most important of these appear to be the ones in which the two chlorine ligands of cisplatin are replaced by purine nitrogen atoms on adjacent bases on the same strand of DNA; these complexes are referred to as 1,2-intrastrand adducts. The purine bases most commonly involved in these adducts are guanines; however, adducts involving one guanine and one adenine are also believed to occur. Generally, the formation of these adducts causes the purines to become destacked and the DNA helix to become kinked.

It is postulated that binding affects both replication and transcription of DNA, as well as mechanisms of DNA repair. The effects of both cisplatin and trans platinum on DNA replication have been studied both in vitro (using cell extracts outside the host organism) and in vivo (inside the host organism). The mechanism is believed to invoke 1,2-intrastrand adducts between cisplatin and DNA, which stops all polymerases from processing (e.g., replicating and transcribing) DNA.

In order to overcome the problem of tumor resistance to known platinum compounds, other platinum compounds need to be developed that damage DNA radically differently than the classical cross-linkers. Novel types of cytotoxic lesions may evade the cellular DNA repair machinery and/or trigger cancer cell death by alternate mechanisms at the genomic level.

Unlike the clinical cross-linking agents, it would be desirable to develop compounds that damage DNA by a dual mechanism involving monofunctional platinum binding to guanine or adenine, and intercalation of certain moieties on compounds into the base pair step adjacent to the site of platination. Accordingly, it would also be desirable to develop compounds that do not mimic the action of cisplatin.

It would be desirable to develop compounds that show a strong cytotoxic effect in a broad range of solid tumors in vitro similar, or superior, to that of the presently available clinical drugs. It would be desirable to develop compounds that prove effective against NSCLC cell lines of different genetic backgrounds. Modifications can be made to the linker geometry, the spectator ligands on the metal center, and/or intercalating portions of the molecule.

The present invention discloses the groundbreaking discovery of alternative platinum based compounds that have a dramatic effect on the treatment of various types of cancer by employing unique biocoordination chemistry leading to heretofore unseen biological activity. Moreover, the newly designed compounds of the present invention are the first examples of hybrid agents that are able to slow progression of an inherently resistant form of cancer in vivo.

BRIEF SUMMARY OF THE INVENTION

The compounds of the present invention are dual platinating/intercalating DNA binders that, unlike clinical platinum agents, do not induce DNA cross-links. The compounds of the present invention lead to greatly enhanced cytotoxicity in several different types of cancers including effectiveness in H460 non-small cell lung cancer (NSCLC) cells, effectiveness against leukemia, and effective tumor growth inhibition in xenograft models.

BRIEF DESCRIPTION OF THE SEVERAL VIEWS OF THE DRAWINGS

FIG. 4 (A) shows the sequence of the 40-base-pair probe with the EcoRI restriction site highlighted. The asterisk denotes the radioactive label. FIGS. 4 (B,C) show denaturing polyacrylamide gels for the enzymatic digestion of DNA incubated for the indicated time intervals at a drug-to-nucleotide ratio of 0.1 at 37° C. with 11 (a comparative compound) and 14a (a compound of the present invention), respectively. The lanes labeled 'uncut' and 'cut' are controls for the undigested and digested unplatinated 40-mer, respectively. Bands are labeled 'f.-1.' for the full-length form and 'cl.' for the cleaved 18-nucleotide fragment. The band of intermediate mobility labeled 'cl.*', which disappears upon addition of NaCN to the mixture prior to electrophoretic separation (not shown), was assigned to platinum-modified cleaved product. FIG. 4 (D) shows time course of EcoRI inhibition as the result of DNA damage by 11 (a comparative compound) shown by open circles and 14a (a compound of the present invention) shown by filled circles based on relative integrated band intensities (arbitrary units) determined densitometrically for the full-length form. Plotted data represent the mean±S.D. of three individual experiments for each complex.

FIG. 5 (A) shows phosphorimage of the sequencing gel showing inhibition of primer extension by Taq DNA polymerase resulting from platination of nucleobases. Lane assignments (from left to right): untreated damage control (ct); T, A, G, and C dideoxy sequencing lanes, giving the sequence on the platinum-modified template (bottom) strand, which reads 5' to 3' from top to bottom of the gel; lanes showing the PCR products resulting from Taq pol inhibition by adducts formed by 11 (a comparative compound), 14a (a compound of the present invention), and cisplatin (cp) on the template strand. Asterisks and arrows indicate characteristic stop sites for cisplatin and complex 14a (a compound of the present invention), respectively. FIG. 5 (B) shows sequence of the 221-base-pair restriction fragment with characteristic damage sites for cisplatin underlined and sequences targeted by complex 14a (a compound of the present invention) highlighted in bold, italicized letters.

DETAILED DESCRIPTION OF THE INVENTION

Figure 1:
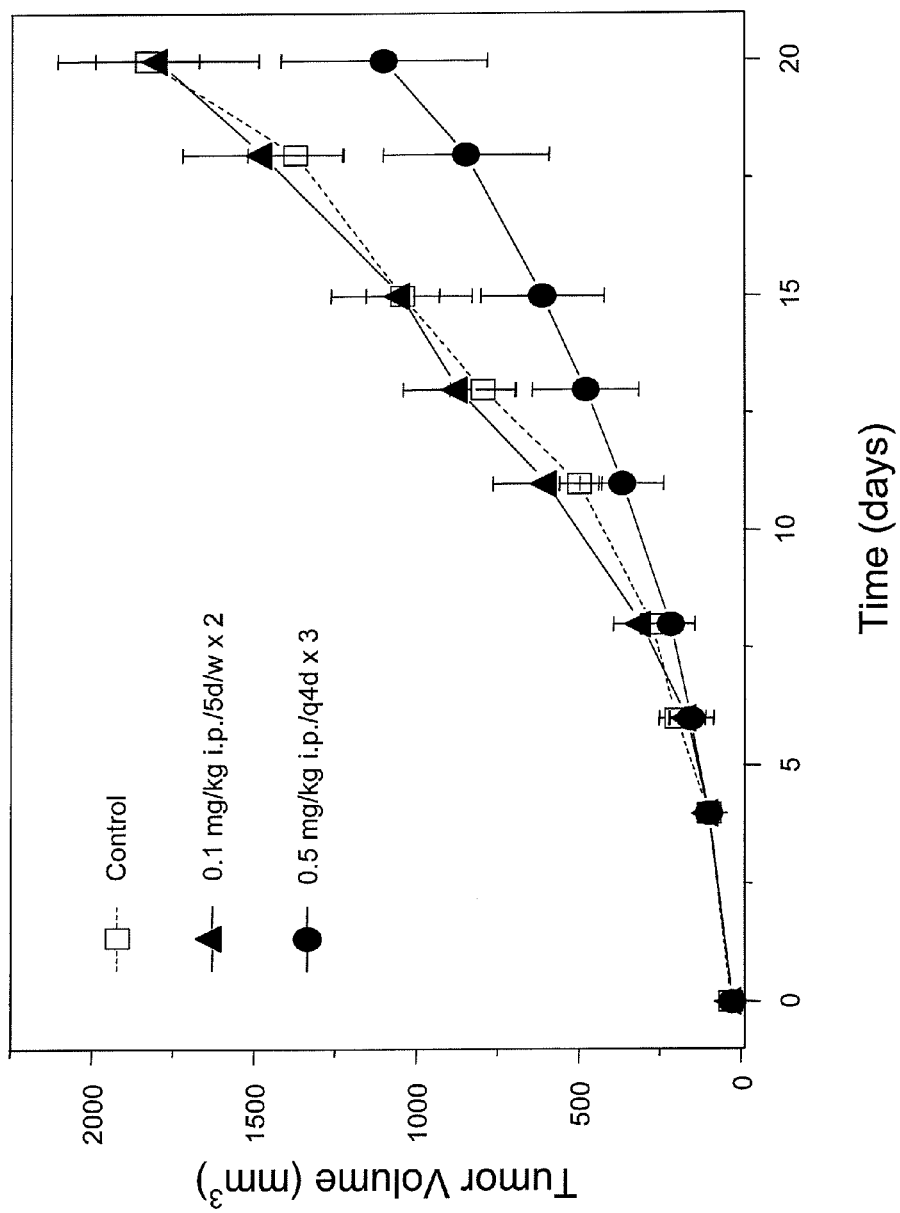
FIG. 1 shows the effect of 14b (a compound of the present invention) on H460 NSCLC tumors xenografted into nude mice. Growth curves are shown for untreated control animals (open squares), and mice treated according to schedule A (filled triangles) and schedule B (filled circles).
Figure 2:
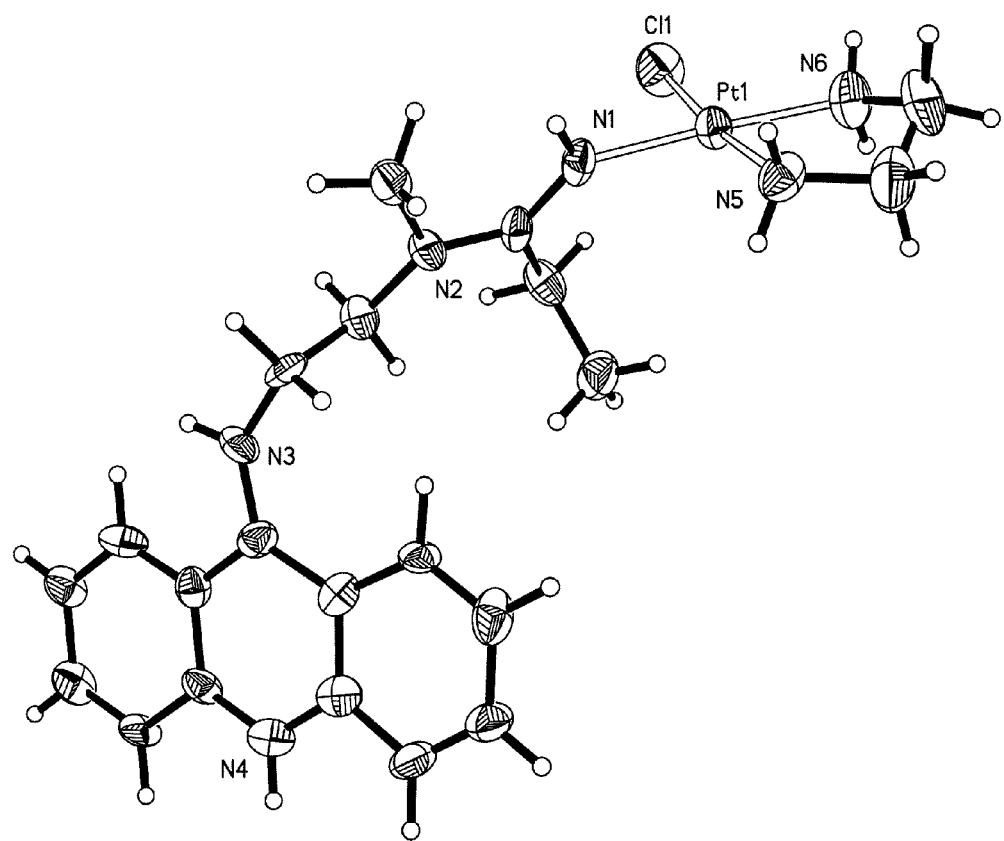
FIG. 2 shows the molecular structure derived from an x-ray structure of one of the compounds of the present invention with selected atoms labeled.
Figure 3:
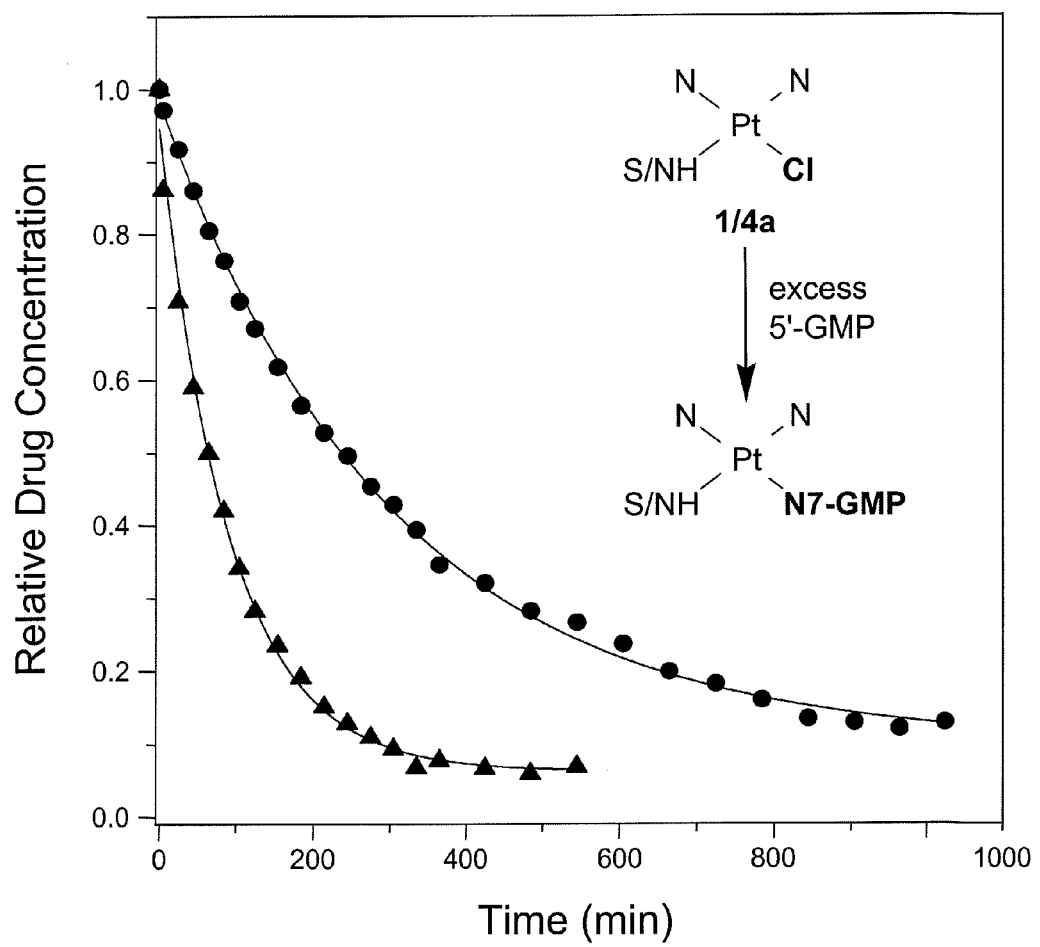
FIG. 3 shows the progress of the reaction of 11 (a comparative compound) with circles and 14a (a compound of the present invention) with triangles with the mononucleotide 5''-GMP at 37° C. monitored by $^1$H NMR spectroscopy. The inset shows a scheme of the reaction monitored. The data plotted is the mean of two experiments.
Figure 4:
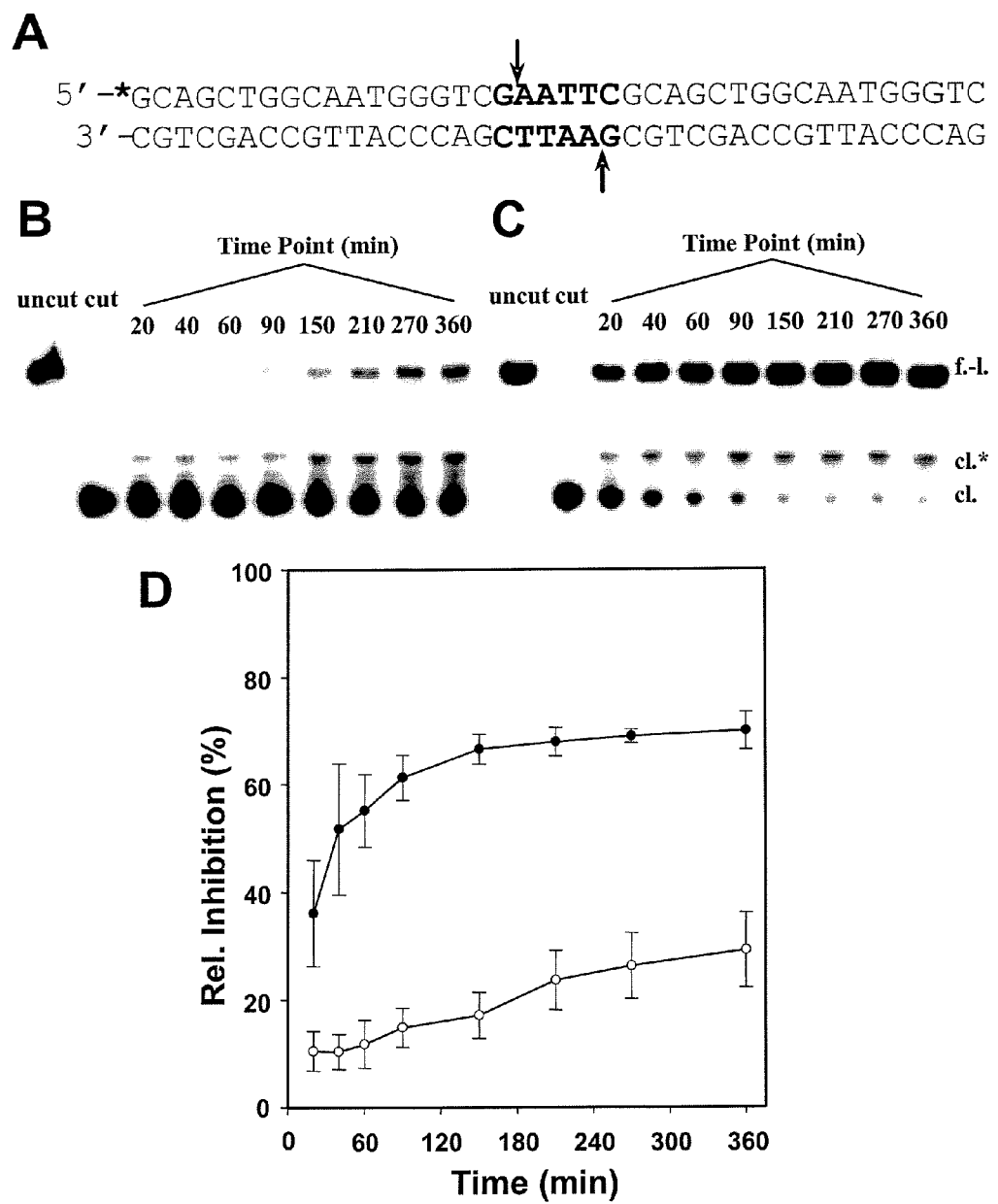
FIG. 4 shows DNA binding efficiency of 11 (a comparative compound) and 14a (a compound of the present invention) monitored by a restriction enzyme cleavage inhibition assay.
Figure 5:
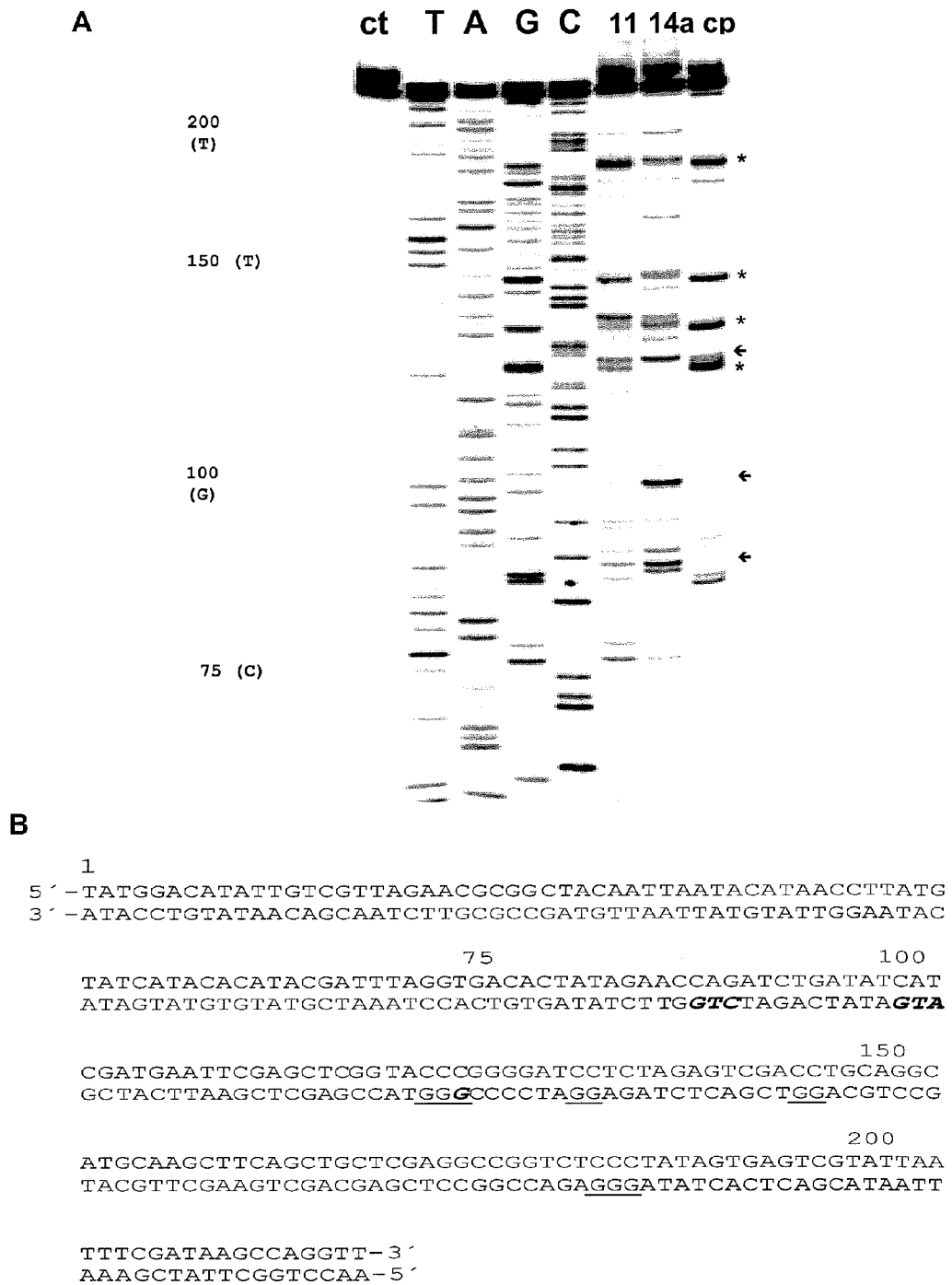
FIG. 5 shows DNA polymerase inhibition assay for detection of DNA damage caused by 11 (a comparative compound), 14a (a compound of the present invention), and cisplatin.

To overcome the problem of tumor resistance to platinum drugs, agents that damage DNA radically differently than the classical cross-linkers have been designed. The rationale behind the approach of the compounds described herein is that novel types of cytotoxic lesions may evade the cellular DNA repair machinery and/or trigger cancer cell death by alternate mechanisms at the genomic level. Platinum-acridinylthiourea conjugates, represented by the prototype, [PtCl(en)(ACRAMTU-S)](NO$_3$)$_2$ (1) ("PT-ACRAMTU"; en=ethylenediamine, ACRAMTU=1-[2-(acridin-9-ylamino) ethyl]-1,3-dimethylthiourea), are a class of cationic DNA-targeted hybrid agents designed toward this goal. Unlike clinical cross-linking agents (and without being bound by the proposed mechanism), the compounds of the present invention damage DNA by a dual mechanism involving monofunctional platinum binding to guanine or adenine, and intercalation of the acridine moiety into the base pair step adjacent to the site of platination. These adducts and the structural perturbations they produce in DNA do not mimic cisplatin's. Thus, the compounds of the present invention are effective against certain cancers that traditional cisplatin compounds are not. Thus, in an embodiment of the present invention it is contemplated and therefore within the scope of the invention that combination therapy can be used including using the compounds of the present invention along with compounds that act by a different mechanism such as more traditional first generation cisplatin compounds and their derivatives. Other combination therapies are contemplated by using those compounds known by those of skill in the art and/or those disclosed and discussed infra.

Despite its charged nature and inability to induce DNA cross-links, two features violating the classical chemical requirements for antitumor activity in cisplatin-type complexes, the compounds of the present invention show a strong cytotoxic effect in a broad range of solid tumors in vitro similar, or superior, to that of known clinical drugs. The thiourea derivative compound's cytotoxicity did not translate into inhibition of tumor growth in vivo. This discrepancy prompted several structure-activity relationship (SAR) studies with the ultimate goal of generating an analogue endowed with clinically useful antitumor activity. Modifications were made to the linker geometry, the spectator ligands on the metal center and the intercalating portion of the molecule. However, none of the derivatives showed a major advantage over the thiourea acridine compound and some of the modifications compromised the compounds' aqueous solubility. After diligent and laborious work, one chemical modification shows a dramatic effect on the biocoordination chemistry and biological activity of this type of conjugate: the replacement of the thiourea sulfur with an amidine nitrogen as the donor atom connecting the metal and intercalator moieties. The newly designed amidine compounds are the first example of this type of hybrid agent able to slow progression of an inherently resistant form of cancer in vivo.

The present invention discloses a plurality of compounds that can be used to treat cancer. These acridine containing platinum compounds have been shown to be effective against a particularly virulent strain of cancer that other platinum containing compounds are unable to treat.

In one embodiment, the compounds that are within the scope of the present invention are defined by Formula I.

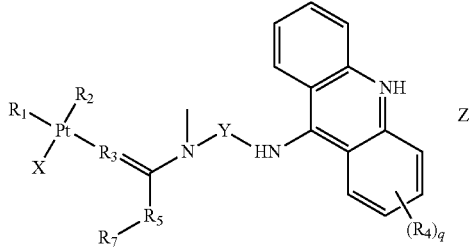

Formula I wherein X is halo, OC(O)R$_9$, nitrate or sulfate;

R$_1$ and R$_2$ are amino groups or together with the platinum atom to which they are attached, R$_1$ and R$_2$ form the ring —NH$_2$—(CH$_2$)$_v$—NH$_2$—wherein v is 1, 2, or 3, or R$_1$ and R$_2$ together can be any of the following groups a-h or R$_1$ and R$_2$ independently can be any of i-m;

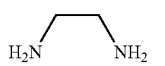   a

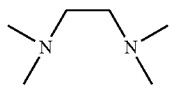   b

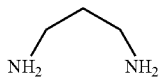   c

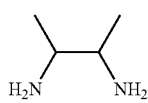   d

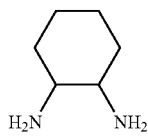   e

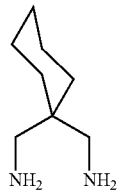   f

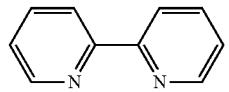   g

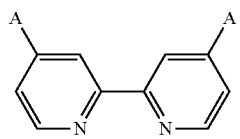   h

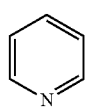   i

NH$_3$   j

NH$_2$R$_{13}$   k

NH(R$_{13}$)$_2$   l

N(R$_{13}$)$_3$   m wherein A is H, —CH$_3$, —OCH$_3$, CF$_3$ or NO$_2$;

R$_{13}$ is independently C$_1$-C$_6$allyl;

R$_3$ is —N(R$_6$)—; wherein R$_6$ is hydrogen or C$_1$-C$_6$alkyl;

R$_4$ is independently an amino, a nitro, —NHC(O)(R$_{10}$), —C(O)NHR$_{10}$, or halo;

R$_{10}$ is hydrogen, C$_{1-6}$ alkyl, phenyl, naphthyl, C$_{3-6}$ cycloalkyl, norbornyl, or adamantyl;

q is 0, 1, or 2;

R$_5$ is a direct bond, —NH— or C$_1$-C$_6$alkylene;

or R$_5$ and X together with the atoms to which they are attached form a 6- or 7-membered ring, wherein said 6- or 7-membered ring contains a linking group —C(O)O— or —OC(O)—;

R$_7$ is hydrogen, methyl, or —C(O)O—R$_8$; wherein

R$_8$ is hydrogen, C$_{1-6}$ alkyl, phenyl, naphthyl, C$_{3-6}$ cycloalkyl, norbornyl, adamantyl, a natural or unnatural amino acid or a peptide;

R$_9$ is hydrogen, C$_{1-6}$ alkyl, phenyl, naphthyl, C$_{3-6}$ cycloalkyl, norbornyl, adamantyl, a natural or unnatural amino acid or a peptide;

Y is C$_1$-C$_6$allylene; and

Z is one or more counterions sufficient to balance the charge of the compound.

In an alternate embodiment, the compounds of the present invention include the compounds of Formula II:

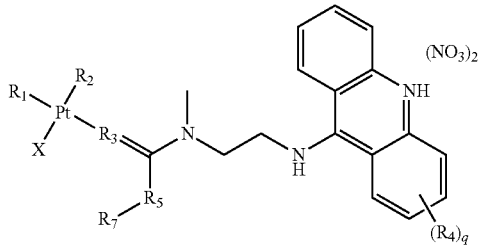

Formula II wherein X is halo, —OC(O)$R_9$, nitrate or sulfate;

$R_1$ and $R_2$ are amino groups or together with the platinum atom to which they are attached, $R_1$ and $R_2$ form the ring —$NH_2$—$(CH_2)_v$—$NH_2$— wherein v is 1, 2, or 3, or $R_1$ and $R_2$ together can be any of the following groups a-h or $R_1$ and $R_2$ independently can be any of i-m;

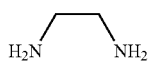 a

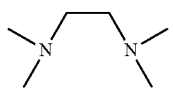 b

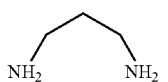 c

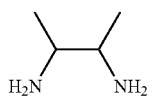 d

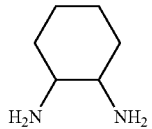 e

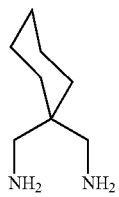 f

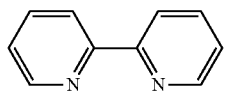 g

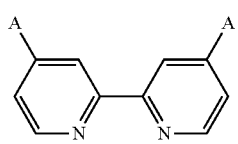 h

 i

 $NH_3$ j

 $NH_2R_{13}$ k

 $NH(R_{13})_2$ l $N(R_{13})_3$ m wherein A is H, —$CH_3$, —$OCH_3$, $CF_3$ or $NO_2$;

$R_{13}$ is independently $C_1$-$C_6$alkyl $R_3$ is —N($R_6$)—, wherein $R_6$ is hydrogen or $C_1$-$C_6$alkyl;

$R_4$ is independently an amino, a nitro, —NHC(O)($R_{10}$), —C(O)NH$R_{10}$, or halo;

$R_{10}$ is hydrogen, $C_{1-6}$ alkyl, phenyl, naphthyl, $C_{3-6}$ cycloalkyl, norbornyl, or adamantyl;

q is 0, 1, or 2;

$R_5$ is a direct bond, —NH— or $C_1$-$C_6$alkylene;

or $R_5$ and X together with the atoms to which they are attached form a 6- or 7-membered ring, wherein said 6- or 7-membered ring contains a linking group —C(O)O— or —OC(O)—;

$R_7$ is hydrogen, methyl, or —C(O)O—$R_8$; wherein $R_8$ is hydrogen, $C_{1-6}$ alkyl, phenyl, naphthyl, $C_{3-6}$ cycloalkyl, norbornyl, or adamantyl, a natural or unnatural amino acid or a peptide;

$R_9$ is hydrogen, $C_{1-6}$ alkyl, phenyl, naphthyl, $C_{3-6}$ cycloalkyl, norbornyl, or adamantyl.

In a further embodiment, the present invention is directed to compounds of Formula III:

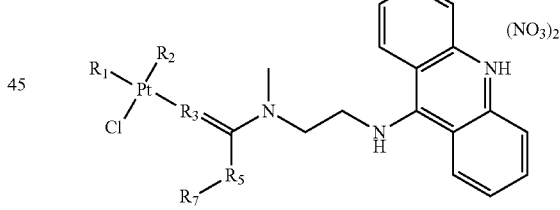

Formula III wherein $R_1$ and $R_2$ are amino groups or together with the platinum atom to which they are attached, $R_1$ and $R_2$ form the ring —$NH_2$—$(CH_2)_v$—$NH_2$— wherein v is 1, 2, or 3, or $R_1$ and $R_2$ together can be any of the following groups a-h or $R_1$ and $R_2$ independently can be any of the following groups 1-171;

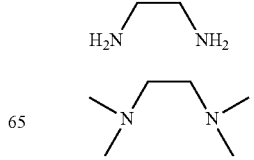

a b

-continued

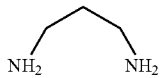
c

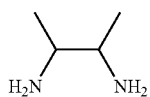
d

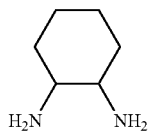
e

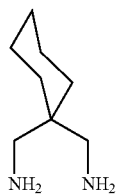
f

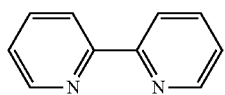
g

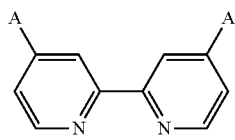
h

i

NH₃  j

NH₂R₁₃  k

NH(R₁₃)₂  l

N(R₁₃)₃  m wherein A is H, —CH₃, —OCH₃, CF₃ or NO₂;
R₁₃ is independently C₁-C₆alkyl
R₃ is —N(R₆)—, wherein R₆ is hydrogen or C₁-C₆alkyl;
R₄ is independently an amino, a nitro, —NHC(O)(R₁₀), —C(O)NHR₁₀, or halo;
R₁₀ is hydrogen, C₁₋₆ alkyl, phenyl, naphthyl, C₃₋₆ cycloalkyl, norbornyl, or adamantyl;
q is 0, 1, or 2;
R₅ is a direct bond, —NH— or C₁-C₆alkylene;
or R₅ and X together with the atoms to which they are attached form a 6- or 7-membered ring, wherein said 6- or 7-membered ring contains a linking group —C(O)O— or —OC(O)—;
R₇ is hydrogen, methyl, or —C(O)O—R₈; wherein
R₈ is hydrogen, C₁₋₆ alkyl, phenyl, naphthyl, C₃₋₆ cycloalkyl, norbornyl, or adamantyl, a natural or unnatural amino acid or a peptide;
R₉ is hydrogen, C₁₋₆ alkyl, phenyl, naphthyl, C₃₋₆ cycloalkyl, norbornyl, or adamantyl.
C₁-C₆alkylene means both straight chain and branched alkylene moieties. For example C₁-C₆alkylene and C₁-C₆alkyl respectively include but are not limited to methylene, methyl, ethylene, ethyl, propylene, propyl, isopropylene, isopropyl, butylene, butyl, isobutylene, isobutyl, t-butylene, t-butyl, and other similar functionalities. Moreover, in all Formula that have an R₅ as part of the Formula, R₅ and the R₇ group that is attached to it can form any straight chain or branched alkyl group that has between 1 and 7 carbon atoms, such as methyl, ethyl, propyl, isopropyl, butyl, isobutyl, t-butyl, and the other similar moieties.

Natural and unnatural amino acids include the twenty one amino acids that are coded for naturally as well as derivatives of those amino acids. These include alanine, cysteine, aspartic acid, asparagine, glutamic acid, glutamine, phenylalanine, glycine, histidine, isoleucine, lysine, leucine, methionine, arginine, proline, serine, threonine, selenocysteine, valine, tryptophan, tyrosine, dimethyl glycine, ornithine, S-adenosylmethionine, canavanine, mimosine, 5-hydroxytryptophan, L-dihydroxyphenylalanine, Eflornithine, 2-aminoisobutyric acid, lanthionine, pyrrolysine. In an embodiment, the natural and unnatural amino acids include dimethyl glycine, alanine, phenylalaine and proline.

A peptide means a 2 to 10 mer of any combination of the amino acids listed above including any duplicates, triplicates, etc.

The natural and unnatural amino acids can be bonded either by the amino functionality or the carboxylate moiety.

It is contemplated and therefore within the scope of the invention that other zwitterionic functionalities can be used in place of the amino acids listed above.

In a variation of the embodiment, compounds of the present invention include Example 1 (note that this is the same compound as compound 14b).

Example 1

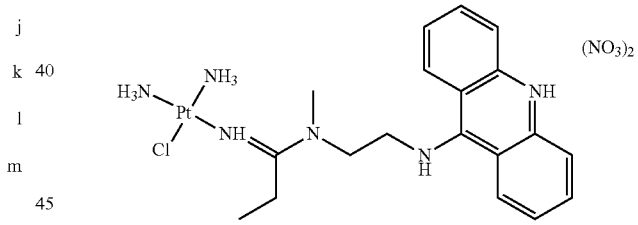

In a variation of the embodiment, compounds of the present invention include Example 2 (note that this is the same compound as compound 14a).

Example 2

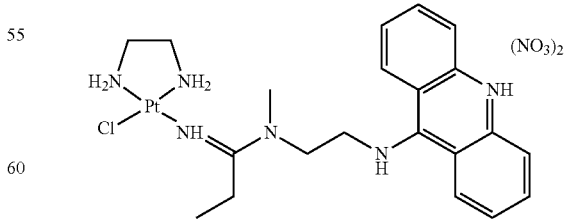

General Preparative Method:
N-(acridin-9-yl)-N'-methylethane-1,2-diamine ("9-acridine-amine") is a common precursor that can be used to make the compounds of the present invention.

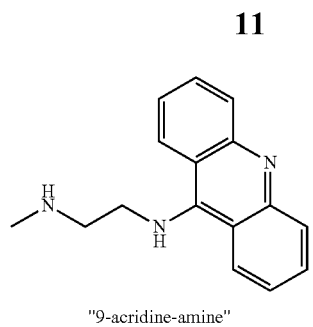

"9-acridine-amine"

Chloro ligand(s) in platinum precursors can be substituted with propionitrile (EtCN). Subsequently, one equivalent of 9-acridine-amine is added to the intermediate to yield a platinum-amidine conjugate through an addition reaction to a metal-activated CN triple bond. For the synthesis of PT-AC-RAMTU analogues, another equivalent of nitric acid can be added to the monocationic nitrate salts to mimic the PT-ACRAMTU dinitrate salt.

A general synthetic methodology and a generic procedure for making the compounds of the present invention are shown in below scheme 1.

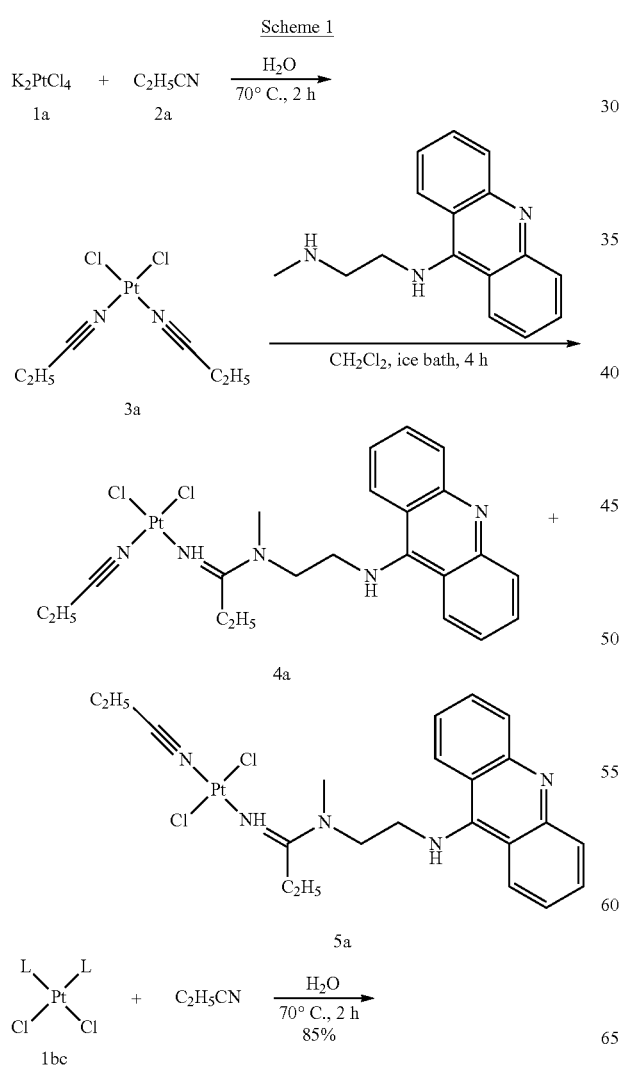

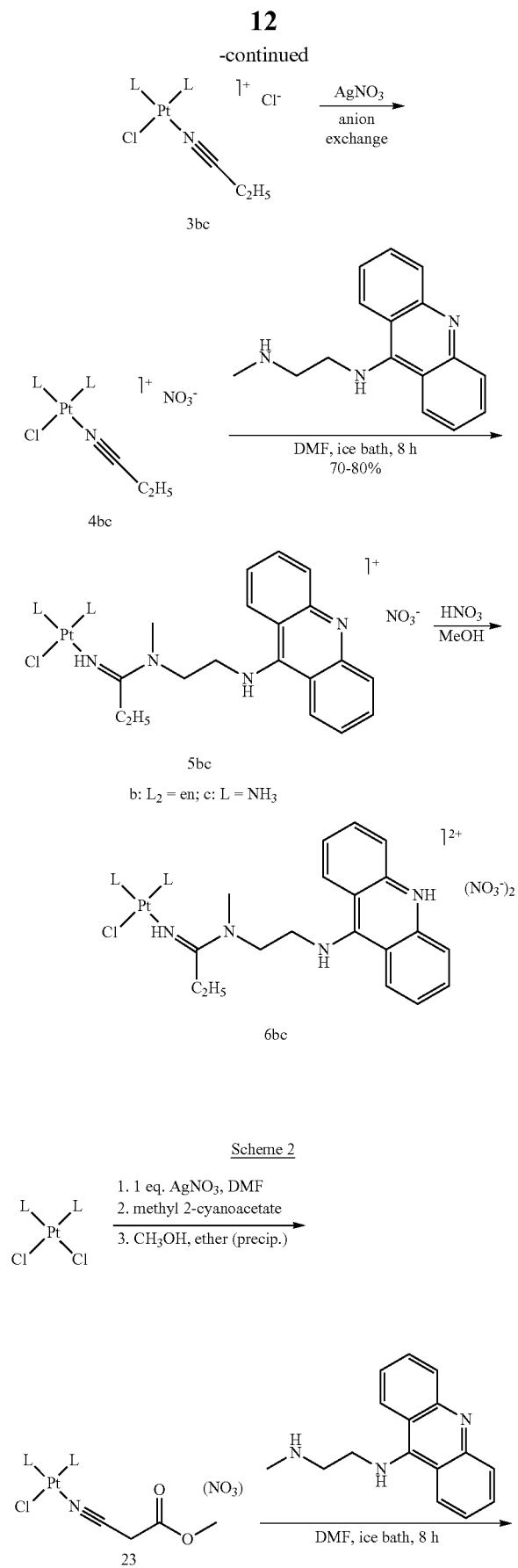

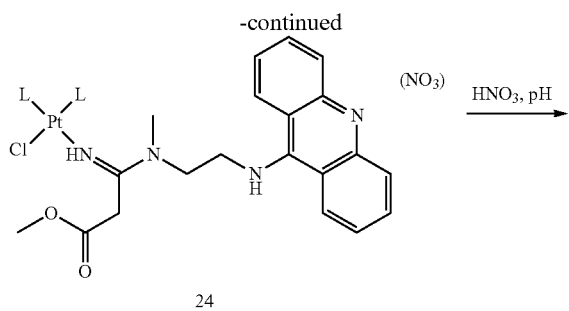

24

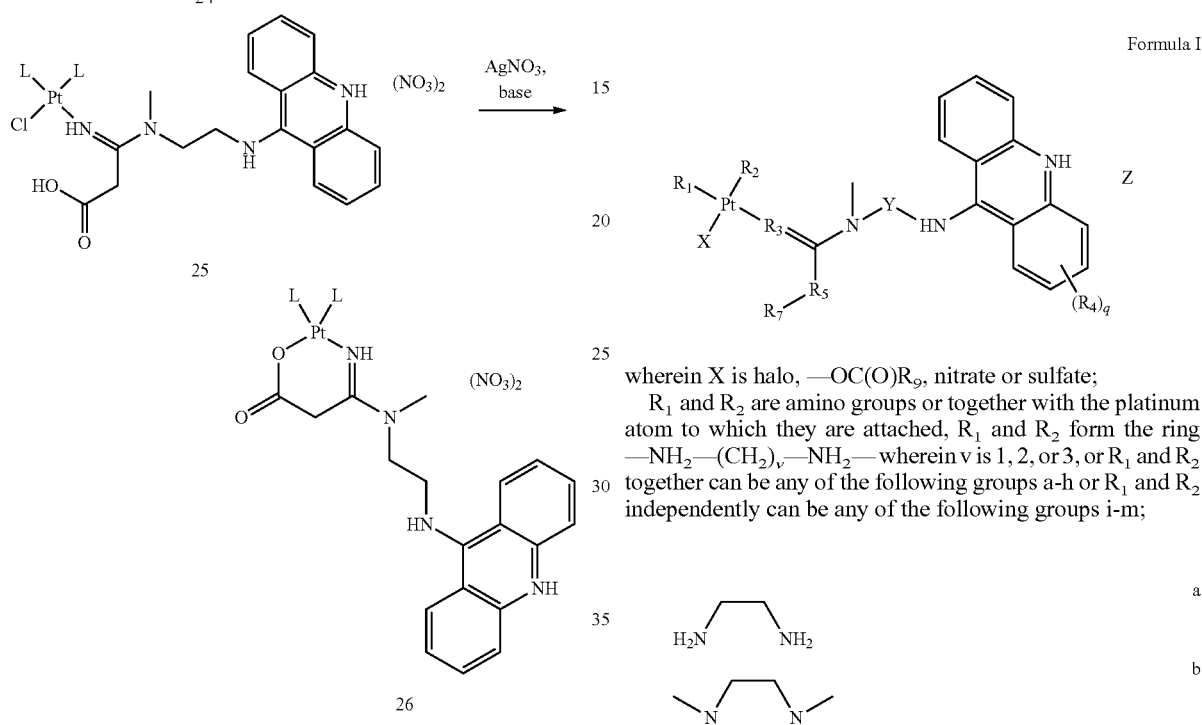

The upper part of scheme 1 shows the methodology development for a synthetic scheme to generate mixtures of the cis and trans isomers of the acridinyl platinum compound. The lower synthetic scheme shows a synthetic methodology combining the acridinyl moiety to the platinum moiety to generate as the principal product the cis isomer of the acridinyl platinum compound.

In the upper synthetic process of scheme 1, the tetrachloro platinum compound 1a is treated with ethyl nitrile to generate the bis cis-chloro bis N-linked propynyl compound 3a. Treatment with an acridinyl substituent generates a mixture of the trans and cis (bis chloro) isomers of the acridinyl platinum compound (compounds 4a and 5a).

Alternatively, in the lower synthetic scheme of scheme 1, the starting material is the bis cis chloro platinum compound that has alternative ligands that allow synthesis of the cis platinum acridinyl compound 6bc. In this synthetic process, the bis cis chloro platinum starting compound 1bc is reacted with the propionitrile compound 2bc to generate the cis mono chloro mono N-linked propionitrile compound 4bc. Compound 4bc is subsequently reacted with an acridinyl compound to generate the acridinyl platinum 5bc, which when done in the presence of nitrous acid results in the cis acridinyl platinum salt represented by compound 6bc.

In scheme 2, it is shown how one can make a 6- or 7-membered compound 26. In scheme 2, one starts with bis cis chloro platinum compound and one uses one equivalent to generate the mono nitrile ester compound 23. To the mono nitrile ester compound 23, one adds the diamino acridine group to generate compound 24. Treatment with acid yields the corresponding acid functionality as shown in compound 25. Finally cyclization occurs to generate the 6-membered lactone ring as shown in compound 26.

The above synthetic schemes can generally be followed to generate the compounds of the present invention. In one embodiment, the synthetic schemes can be used to generate the compounds of Formula I:

Formula I wherein X is halo, —OC(O)R$_9$, nitrate or sulfate;

R$_1$ and R$_2$ are amino groups or together with the platinum atom to which they are attached, R$_1$ and R$_2$ form the ring —NH$_2$—(CH$_2$)$_v$—NH$_2$—wherein v is 1, 2, or 3, or R$_1$ and R$_2$ together can be any of the following groups a-h or R$_1$ and R$_2$ independently can be any of the following groups i-m;

a

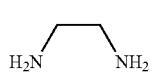

b

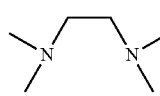

c

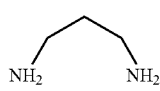

d

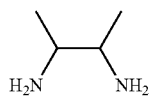

e

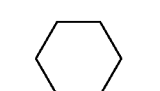

f

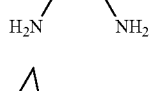

g

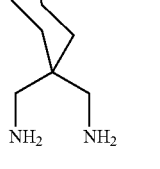

-continued

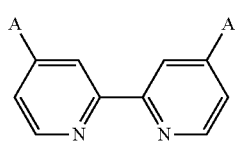
h

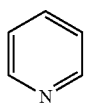
i

NH$_3$ j

NH$_2$R$_{13}$ k

NH(R$_{13}$)$_2$ l

N(R$_{13}$)$_3$ m wherein A is H, —CH$_3$, —OCH$_3$, CF$_3$ or NO$_2$;

R$_{13}$ is independently C$_1$-C$_6$alkyl;

R$_3$ is —N(R$_6$)—, wherein R$_6$ is hydrogen or C$_1$-C$_6$alkyl;

R$_4$ is independently an amino, a nitro, —NHC(O)(R$_{10}$), —C(O)NHR$_{10}$, or halo;

R$_{10}$ is hydrogen, C$_{1-6}$ alkyl, phenyl, naphthyl, C$_{3-6}$ cycloalkyl, norbornyl, or adamantyl;

q is 0, 1, or 2;

R$_5$ is a direct bond, —NH— or C$_1$-C$_6$alkylene;

or R$_5$ and X together with the atoms to which they are attached form a 6- or 7-membered ring, wherein said 6- or 7-membered ring contains a linking group —C(O)O— or —OC(O)—;

R$_7$ is hydrogen, methyl, or —C(O)O—R$_8$; wherein

R$_8$ is hydrogen, C$_{1-6}$ alkyl, phenyl, naphthyl, C$_{3-6}$ cycloalkyl, norbornyl, or adamantyl, a natural or unnatural amino acid or a peptide;

R$_9$ is hydrogen, C$_{1-6}$ alkyl, phenyl, naphthyl, C$_{3-6}$ cycloalkyl, norbornyl, or adamantyl;

Y is C$_1$-C$_6$alkylene; and

Z is one or more counterions sufficient to balance the charge of the compound.

In a variation of this embodiment, the following variables may independently be represented as follows:

R$_3$ may be —N(R$_6$)—,

Y may be —CH$_2$—,

R$_1$ and R$_2$ may be amino groups or together with the platinum atom to which R$_1$ and R$_2$ are attached, they may be —NH$_2$—CH$_2$—NH$_2$—, the counter ion Z comprises NO$_3$.

R$_5$ may be —NH— or —CH$_2$—, or R$_5$ and X together with the atoms to which they are attached form a 6- or 7-membered ring, wherein said 6- or 7-membered ring contains a linking group —C(O)O— or —OC(O)—;

R$_7$ is hydrogen, methyl, or —C(O)O—R$_8$; wherein

R$_8$ is hydrogen, C$_{1-6}$ alkyl, phenyl, naphthyl, C$_{3-6}$ cycloalkyl, norbornyl, or adamantyl, a natural or unnatural amino acid or a peptide;

R$_9$ is hydrogen, C$_{1-6}$ alkyl, phenyl, naphthyl, C$_{3-6}$ cycloalkyl, norbornyl, or adamantyl; and R$_6$ may be hydrogen or methyl.

In a variation, the general synthetic scheme can be used to generate the compound shown as Example 1:

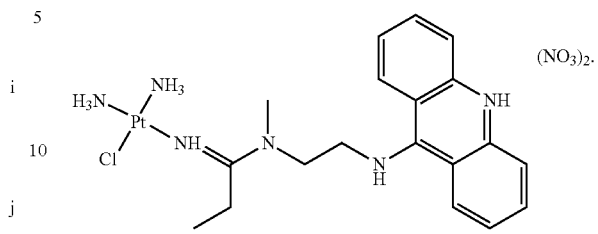

Example 1

In another variation, the general synthetic schemes above can be used to generate the compound that is Example 2:

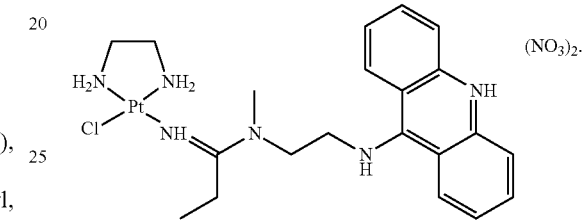

Example 2

In an embodiment, the compounds of the present invention can be used to treat cancer. Thus, in an embodiment, methods of treating cancer comprising administering to a subject in need thereof an effective amount of the compound of Formula I is within the scope of the present invention. In a variation, the methods of treating cancer include leukemia, lung cancer, testicular cancers, ovarian carcinomas, various head and neck cancers, and patients with lymphomas. In a further variation, the methods of treating cancer include leukemia. In a further variation, the methods of treating cancer include non-small cell lung cancer. In a further variation, the methods of treating cancer include cisplatin resistant ovarian cancers.

Synthesis and Characterization of Examples

The synthetic procedure to make Examples 1 and 2 (compounds 14b and 14a) are shown below in scheme 3 and are described in further detail below.

Scheme 3

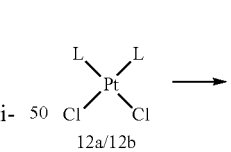
12a/12b

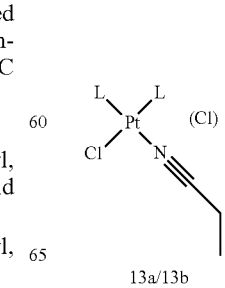
13a/13b

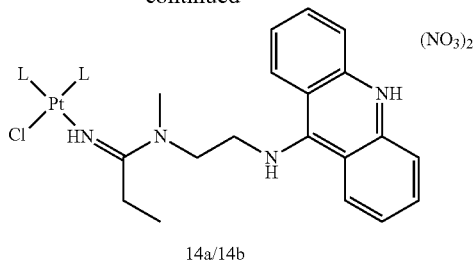

14a/14b a: L2 = en; b = NH₃

Synthesis and Product Characterization. ¹H NMR spectra of the target compounds and intermediates were recorded on Bruker Advance 300 and DRX-500 instruments operating at 500 and 300 MHz, respectively. ¹³C NMR spectra were recorded on a Broker Advance 300 instrument operating at 75.5 MHz. Chemical shifts (δ) are given in parts per million (ppm) relative to internal standards trimethylsilane (TMS), or 3-(trimethylsilyl)-1-propanesulfonic acid sodium salt (DSS) for samples in $D_2O$. ¹⁹⁵Pt NMR spectra were recorded on a Bruker DRX-500 MHz spectrometer at 107.5 MHz. Aqueous $K_2$-[PtCl₄] was used as an external standard, and ¹⁹⁵Pt chemical shifts are reported vs $[PtCl_6]^{2-}$. The target compounds (Example 1 and Example 2) were fully characterized by gradient COSY and ¹H-detected gradient HMQC and HMBC spectra recorded on a Bruker DRX-500 MHz spectrometer. Elemental analyses were performed by Quantitative Technologies Inc., Madison, N.J. All reagents were used as obtained from commercial sources without further purification unless indicated otherwise. Solvents were dried and distilled prior to use.

Synthesis of complex 13 *a* (from Scheme 3 ). The complex [PtCl₂(en)] (200 mg, 0.613 mmol) was heated under reflux in dilute HCl (pH 4) with propionitrile (2.7 mL, excess) until the yellow suspension turned into a colorless solution (~2 h). Solvent was removed by rotary evaporation, and the pale yellow residue was dissolved in 7 mL of dry methanol. The solution was passed through a syringe filter, and the colorless filtrate was added directly into 140 mL of vigorously stirred dry diethyl ether, affording 13a as an off-white microcrystalline precipitate, which was filtered off and dried in a vacuum. Yield 210 mg (90%). ¹H NMR ($D_2O$) δ 2.88 (2H, q, J=7.5 Hz), 2.64 (4H, m), 1.30 (3H, t, J=7.5 Hz). ¹³C—{H} NMR ($D_2O$) δ122.9, 48.7, 48.4, 12.3, 9.2. ¹⁹⁵Pt NMR ($D_2O$) δ−2711. Anal. ($C_5H_{13}Cl_2N_3Pt$) C, H, N.

Synthesis of complex 13 *b* (from Scheme 3). This precursor was synthesized analogously to 13a starting from [PtCl₂(NH₃)₂] (300 mg, 1 mmol) and propionitrile (4.2 mL). Yield: 295 mg (83%). ¹H NMR ($D_2O$) δ 2.89 (2H, q, J=7.5 Hz), 1.31 (3H, t, J=7.5 Hz). ¹³C—{H} NMR ($D_2O$) δ121.9, 12.3, 9.2. ¹⁹⁵Pt NMR ($D_2O$) δ 2467. Anal. ($C_3H_{11}Cl_2N_3Pt$) C, H, N.

Complexes 13 *a'* and 14 *a'* (isotopically enriched 13*a* and 14 *a*) containing ¹⁵N-en were synthesized accordingly starting from [PtCl₂(¹⁵N-en)]. 13*a'*: ¹H NMR (MeOH-d₄): δ 6.11 and 5.86 (2H, d of t, NH₂ trans to Cl, ¹J(¹H-¹⁵N)=75 Hz, ³J(¹H-¹H)=5.3 Hz), 6.01 and 5.76 (2H, d of t, NH₂ trans to N, ¹J(¹H—¹⁵N)=75 Hz, ³J(¹H-¹H)=5.2 Hz), 2.93 (2H, q, J=7.6 Hz), 2.57 (4H, m), 1.33 (3H, t, J=7.5 Hz). 14a': ¹H NMR (DMF-d₇) 813.92 (1H, s), 9.90 (1H, s), 8.70 (2H, d, J=8.6 Hz), 8.07 (4H, m, overlap), 7.63 (2H, t, J=6.8 Hz), 6.26 (NH, 1H, s), 5.82 and 5.53 (2H, d of t, NH₂ trans to Cl, ¹J(¹H-¹⁵N)=74.5 Hz, ³J(¹H—¹H)=5.0 Hz and 5.1 Hz), 5.47 (2H, d of t, NH₂ trans to N, ¹J(¹H-¹⁵N)=75 Hz, ³J(¹H-¹H)=5.1 Hz), 4.51 (2H, t, J=6.3 Hz), 4.10 (2H, t, J=6.7 Hz), 3.21 (3H, s), 3.12 (2H, q, J=7.4 Hz), 2.68 (4H, s), 1.33 (3H, t, J=7.5 Hz).

Synthesis of Complex 14*a* (from Scheme 3 ). Precursor complex 13a (170 mg, 0.45 mmol) was converted to its nitrate salt by reaction with AgNO₃ (75 mg, 0.44 mmol) in 10 mL of anhydrous DMF. AgCl was filtered off, and the filtrate was cooled to −10° C. N-(acridin-9-yl)-N"-methylethane-1,2-diamine (117 mg, 0.47 mmol) was added to the solution, and the suspension was stirred until it turned into an orange-red solution (~7 h). The reaction mixture was added dropwise into 200 mL of cold dichloromethane, and the resulting yellow slurry was vigorously stirred for 30 min. The precipitate was recovered by membrane filtration, dried in a vacuum overnight, and dissolved in 40 mL of methanol containing 1 mol equiv of HNO₃. After removal of the solvent by rotary evaporation, the crude product was recrystallized from hot ethanol, affording 14a as a microcrystalline solid. Yield 169 mg (52%). ¹H NMR (DMF-d₇) δ 13.92 (1H, s), 9.90 (1H, s), 8.70 (2H, d, J=8.6 Hz), 8.07 (4H, over 1 m), 7.63 (2H, t, J=6.8 Hz), 5.78 (2H, s), 5.48 (2H, s), 4.51 2H, t, J=6.3 Hz), 4.10 (2H, t, J=6.7 Hz), 3.21 (3H, s), 3.12 (2H, q, J=7.4 Hz), 2.68 (4H, s), 1.33 (3H, t, J=7.5 Hz). ¹³C—{H} NMR (DMF-d₇) δ 170.4, 159.0, 140.6, 135.7, 128.2, 124.3, 119.4, 113.5, 50.1, 49.4, 49.2, 47.5, 28.0, 11.4. ¹⁹⁵Pt NMR (DMF-d₇) δ−2494. UV/Vis ($H_2O$): λ$_{max}$ 413, ε=10571. Anal. ($C_{21}H_{31}ClN_8O_6Pt.H_2O$)C, H, N.

Synthesis of Complex 14*b* (from Scheme 3): This analogue was prepared as described for 14*a* starting from 293 mg (0.83 mmol) of 13*b*, 132 mg (0.79 mmol) of AgNO₃, and 197 mg (0.79 mmol) of N-(acridin-9-yl)-N'-methylethane-1,2-diamine. Yield: 315 mg (57%). ¹H NMR (DMF-d₇) δ 13.93 (1H, s), 9.92 (1H, s), 8.68 (2H, d, J=8.6 Hz), 8.03 (4H, over 1 m), 7.62 (t, J=7.2 Hz), 6.27 (1H, s), 4.53 (3H, s), 4.49 (2H, t, J=6.8 Hz), 4.16 (3H, s), 4.10 (2H, t, J=6.3 Hz), 3.20 (3H, s), 3.15 (2H, q, J=7.6 Hz), 1.33 (3H, t, J=7.5 Hz). ¹³C—{H} NMR (DMF-d₇) δ 170.3, 159.3, 140.8, 135.9, 126.5, 124.5, 119.6, 113.6, 50.8, 47.8, 28.3, 11.5. ¹⁹⁵Pt NMR (DMF-d₇) δ−2264. UV/Vis ($H_2O$): λ$_{max}$ 413 , ε=9224. Anal. ($C_{19}H_{29}ClN_8O_6Pt.2.5H_2O$)C, H, N.

NMR Spectroscopy. NMR spectra in arrayed experiments were collected at 37° C. on a Bruker 500 DRX spectrometer equipped with a triple-resonance broadband inverse probe and a variable temperature unit. Reactions were performed in 5-mm NMR tubes containing 2 mM complex and 6 mM 5'-GMP (10 mM phosphate buffer, $D_2O$, pH* 6.8). 1-D ¹H kinetics experiments were carried out as a standard Bruker arrayed 2-D experiment using a variable-delay list. Incremented 1-D spectra were processed exactly the same, and suitable signals were integrated. Data were processed with XWINNMR 3.6 (Bruker, Ettlingen, Germany). The concentrations of platinum complex at each time point were deduced from relative peak intensities, averaged over multiple signals to account for differences in proton relaxation, and the data were fitted to the equation, $y=A_0 \times e^{-x/t}$ (where $A_0$=1 and $t^{-1}=k_{obs}$), using Origin 7 (OriginLab, Northampton, Mass.). 2-D HMQC experiments were also performed.

In Vitro Studies

Restriction Enzyme Cleavage Assay. The top and bottom strands of a 40-base-pair DNA fragment were synthesized and HPLC-purified by IDT Inc. (Coralville, Iowa). The top strand was radioactively labeled using T4 polynucleotide kinase (EPICENTRE Biotechnologies, Madison, Wis.) and [γ-³²P]ATP (Amersham Biosciences, Piscataway, N.J.) prior to annealing with the complementary strand in reaction buffer (10 mM Tris-HCl, pH 7.5, 50 mM NaCl). Conjugates 11 and 14a were incubated with labeled probe at 37° C. at a drug-to-nucleotide ratio of 0.1, and the samples withdrawn at various time points from the mixtures were treated with thiourea (5-fold the concentration of drug) at 4° C. for 30 min. Unmodified and drug-modified DNA samples were reacted with 60 units of EcoRI (New England Biolabs, Beverly, Mass.) at 37° C. for 40 min in enzyme buffer provided by the vendor. Digested and undigested fragments were separated on polyacrylamide gels (12% acrylamide, 8 M urea) and quantified on a BioRad FX-Pro Plus phosphorimager (Hercules, Calif.) using the BioRad Quantity One software (version 4.4.1).

DNA Polymerase Inhibition Assay. A 221-base-pair NdeI/HpaI restriction fragment from plasmid pSP73 was generated by PCR amplification and purified according to a published protocol. (Guddneppanavar et al. 2007). Appropriate amounts of DNA (10 µg/50 µL) were incubated with complexes 11, 14a, and cisplatin at a drug-to-nucleotide ratio of 0.0075 in 10 mM Tris-HCl (pH 8.0) at 37° C. for 24 h. All other manipulations and experimental conditions of this assay were adopted from previously optimized protocols (Guddneppanavar et al. 2007), including 5' end-labeling of primer, PCR protocols for dideoxy sequencing and footprinting reactions using Taq polymerase (Promega, Madison, Wis.), and details of the gel electrophoresis and documentation.

Cytotoxicity Assay. Cytotoxicity studies were carried out according to a standard protocol (Guddneppanavar et al. 2006) using the Celltiter 96 Aqueous Non-Radioactive Cell Proliferation Assay kit (Promega, Madison, Wis.). Stock solutions of 11, 14a, and 14bwere prepared in phosphate-buffered saline (PBS) and serially diluted with media prior to incubation with cancer cells. $IC_{50}$ values were calculated from non-linear curve fits using a sigmoidal dose-response equation in GraphPad Prism (GraphPad Software, La Jolla, Calif.).

Treatment of Cancer/In Vivo Studies

Xenograft Study. H460 xenografts were established in nude athymic female mice via bilateral subcutaneous injections. Treatment began when the average tumor volume was approximately 100 mm³. The tumor-bearing mice were randomized depending on tumor volume into three groups of five test animals each: one control group receiving vehicle only, one group treated at 0.1 mg/kg 5d/w×2 (A), and one group treated at 0.5 mg/kg q4d×3 (B). Animal weights and tumor volumes were measured and recorded for 17 days after the first dose was administered. Tumor volumes were determined using the formula: $V (mm^3) = d^2 \times D/2$, where d and D are the shortest and longest dimension of the tumor, respectively, and are reported as the sum of both tumors for each test animal. At the end of the study, all animals were euthanized and disposed of according to Standard Operating Procedures (SOPs). Statistical analysis of the growth curves was done using a non-linear polynomial random-coefficient model in SAS Proc Mixed (SAS Institute Inc., Cary, N.C.).

The compounds of the present invention were studied for their cytotoxic effect in the human leukemia cell line, HL-60, and the NSCLC cell line, NCI—H460. The results of the cell proliferation assay are summarized below in Table I.

TABLE 1

Cytotoxicity Data

| Compound | $IC_{50}$ (µM) ± SEM* | |
|---|---|---|
|  | HL-60 | NCI-H460 |
| 11 | 3.95 ± 0.24 | 0.35 ± 0.017 |
| 14a (scheme 3) | 2.97 ± 0.11 | 0.028 ± 0.0024 |
| 14b (scheme 3) | 0.47 ± 0.06 | 0.026 ± 0.0022 |

*Concentrations of compound that reduce cell viability by 50%, determined by cell proliferation assays. Cells were incubated with drug for 72 h. Values are means of four experiments ± the standard error of the mean.

As can be seen from Table 1, in HL-60, the compounds of the present invention showed activity based on IC50 values that were in the micromolar range. All of the compounds of the present invention showed very good activity against the H460 cell line. Compound 11 is shown below.

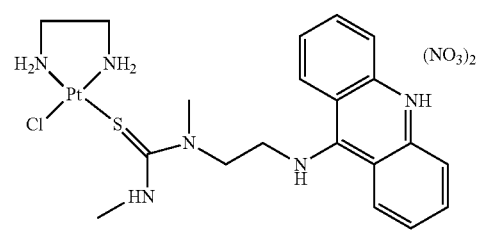

The antitumor activity of compound 14b was evaluated against H460 bilateral tumors implanted into athymic nude mice. Complex 14b was selected for this study, because it was slightly more soluble in biological media than 14a. Complex 14b was administered intraperitonealy (i.p.) according to the following dosing schedules: (A) 0.1 mg/kg, five days per week for two consecutive weeks (5d/w×2), and (B) 0.5 mg/kg, three doses given at 4-day intervals (q4d×3). The tumor volumes recorded in both treatment groups and in untreated control animals are plotted vs. days of treatment in FIG. 1. At the end of the study, the tumors measured 1834±160, 1798±309, and 1102±319 mm³ (means±S.E.M.) for the control animals and animals treated according to schedules A and B, respectively. Based on these data, the low-dose treatment (A) had no effect on tumor growth. However, treatment at the higher dose (B), which is close to the maximum tolerated dose (MTD) of compound 14b, slowed the tumor growth rate significantly (P<0.01) compared to the control group, which led to a reduction in the mean terminal tumor volume by 40%.

FIG. 1 shows the effect of 14b on H460 NSCLC tumors xenografted into nude mice. Growth curves are shown for untreated control animals (open squares), and mice treated according to schedule A (filled triangles) and schedule B (filled circles). Measurement of tumor volumes began on day 0, and treatment began on day 4. Each data point represents the mean of 5 tumor volumes±S.E.M.

Complexes 14a and 14b are remarkably cytotoxic in H460 NSCLC cells. These are two of a very limited number of drugs known to inhibit H460 cell growth with similar potency in the nanomolar concentration range. Cisplatin is at least 20-fold less potent than the non-classical compounds of the present invention in H460 cells with $IC_{50}$ values typically in the micromolar range. The high cell kill potential of the compounds of the present invention in H460 cells translates into pronounced antitumor activity. This was demonstrated for compound 14b in the corresponding tumor xenograft, in which the drug slowed tumor growth at a sublethal dose close to the MTD. The high cytotoxic potency of compound 14b is documented by the fact that it is tolerated at doses an order of magnitude lower than those commonly applied for cisplatin when administered i.p. The new compounds of the present invention show significantly improved cytotoxic potential compared to the 'classical' monofunctional, complex, cis-[Pt(NH$_3$)$_2$(pyridine)Cl]$^+$, which requires high drug doses to produce an appreciable antitumor effect in vivo.

In an embodiment of the present invention, compounds of Formula I are contemplated.

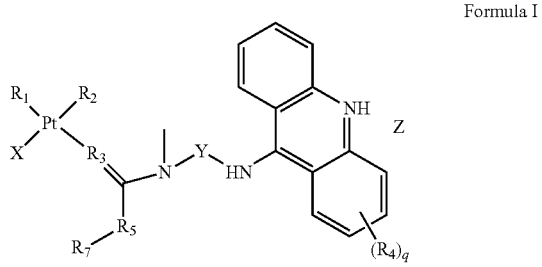

Formula I wherein X is halo, —OC(O)R$_9$, nitrate or sulfate;

R$_1$ and R$_2$ are amino groups or together with the platinum atom to which they are attached, R$_1$ and R$_2$ form the ring —NH$_2$—(CH$_2$)$_v$—NH$_2$— wherein v is 1, 2, or 3;

R$_3$ is —N(R$_6$)—; wherein R$_6$ is hydrogen or C$_1$-C$_6$alkyl;

R$_4$ is independently an amino, a nitro, —NHC(O)(R$_{10}$), —C(O)NHR$_{10}$, or halo;

R$_{10}$ is hydrogen, C$_{1-6}$ alkyl, phenyl, naphthyl, C$_{3-6}$ cycloalkyl, norbornyl, or adamantyl;

q is 0, 1, or 2;

R$_5$ is a direct bond, —NH— or C$_1$-C$_6$alkylene;

or R$_5$ and X together with the atoms to which they are attached form a 6- or 7-membered ring, wherein said 6- or 7-membered ring contains a linking group —C(O)O— or —OC(O)—;

R$_7$ is hydrogen, methyl, or —C(O)O—R$_8$; wherein

R$_8$ is hydrogen, C$_{1-6}$ alkyl, phenyl, naphthyl, C$_{3-6}$ cycloalkyl, norbornyl, or adamantyl, a natural or unnatural amino acid or a peptide;

R$_9$ is hydrogen, C$_{1-6}$ alkyl, phenyl, naphthyl, C$_{3-6}$ cycloalkyl, norbornyl, or adamantyl;

Y is C$_1$-C$_6$alkylene; and

Z is one or more counterions sufficient to balance the charge of the compound.

In an embodiment, the present invention discloses methods of treating cancer in an individual in need thereof by the use of a compound of Formula I.

In a variation, the compounds of the present invention can be used for treating diseases of abnormal cell growth and/or dysregulated apoptosis, such as cancer, mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumors, primary or secondary brain tumors, Hodgkin's disease, chronic or acute leukemias, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblasitoma, or a combination thereof.

In a further variation, the compounds of the present invention can be used in methods of treating mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblasitoma, or a combination of one or more of the above cancers in a patient, said methods comprising administering thereto a therapeutically effective amount of a compound having formula (II).

In a further variation, the compounds of the present invention can be used for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer and spleen cancer.

In a variation of the method, the cancer may alternatively be selected from the group consisting of lung cancer, genitourinal cancers, bladder cancers, testicular cancers, ovarian carcinomas, various head and neck cancers, colon cancers, various leukemias, and various lymphomas.

In another variation of the method, the variables of formula I may be any of the follows:

R$_3$ may be —N(R$_6$)—, wherein R$_6$ is C$_{1-6}$alkyl or hydrogen. In a variation, Y may be —CH$_2$—. In a variation, R$_1$ and R$_2$ may be amino groups or together with the platinum atom to which $R_1$ and $R_2$ are attached are —$NH_2$—$CH_2$—$NH_2$—. In a variation, the counter ion Z comprises $NO_3$. In a further variation, $R_5$ may be —NH— or —$CH_2$—. In a further variation, $R_6$ may be hydrogen or methyl.

In another embodiment, the present invention is directed to a pharmaceutical composition comprising the compound of Formula I:

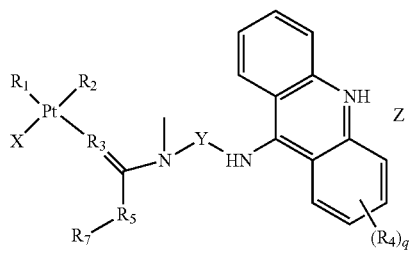

Formula I wherein X is halo, —OC(O)$R_9$, nitrate or sulfate;

$R_1$ and $R_2$ are amino groups or together with the platinum atom to which they are attached, $R_1$ and $R_2$ form the ring —$NH_2$—$(CH_2)_v$—$NH_2$— wherein v is 1, 2, or 3;

$R_3$ is —N($R_6$)—, wherein $R_6$ is hydrogen or $C_1$-$C_6$alkyl;

$R_4$ is independently an amino, a nitro, —NHC(O)($R_{10}$), —C(O)NH$R_{10}$, or halo;

$R_{10}$ is hydrogen, $C_{1-6}$ alkyl, phenyl, naphthyl, $C_{3-6}$ cycloalkyl, norbornyl, or adamantyl;

q is 0, 1, or 2;

$R_5$ is a direct bond, —NH— or $C_1$-$C_6$alkylene;

or $R_5$ and X together with the atoms to which they are attached form a 6- or 7-membered ring, wherein said 6- or 7-membered ring contains a linking group —C(O)O— or —OC(O)—;

$R_7$ is hydrogen, methyl, or —C(O)O—$R_8$; wherein $R_8$ is hydrogen, $C_{1-6}$ alkyl, phenyl, naphthyl, $C_{3-6}$ cycloalkyl, norbornyl, or adamantyl, a natural or unnatural amino acid or a peptide;

$R_9$ is hydrogen, $C_{1-6}$ alkyl, phenyl, naphthyl, $C_{3-6}$ cycloalkyl, norbornyl, or adamantyl;

Y is $C_1$-$C_6$alkylene; and

Z is one or more counterions sufficient to balance the charge of the compound;

and pharmaceutically acceptable diluents, carriers, or excipients.

In a variation, the pharmaceutical composition may have variables that are defined as follows: Y may be —$CH_2$—, $R_1$ and $R_2$ may be amino groups or together with the platinum atom to which $R_1$ and $R_2$ are attached may be —$NH_2$—$CH_2$—$NH_2$—, and wherein the counter ion Z comprises $NO_3$.

In a variation, the pharmaceutical composition optionally has the variables defined as follows: $R_5$ is —NH— or —$CH_2$— and $R_6$ is hydrogen or methyl.

In a further variation, the present invention contemplates combination therapies in which the compounds of the present invention can be used in conjunction with other cisplatin compounds. The efficacy of this combination therapy is likely to be enhanced because of the different mechanisms and modes of action that first generation cisplatin compounds exhibit relative to the compounds of the present invention. It is also contemplated and therefore within the scope of the invention that other anti-neoplastic agents/compounds can be used in conjunction with the compounds of the present invention. The anti-neoplastic agents/compounds that can be used with the compounds of the present invention include cytotoxic compounds as well as non-cytotoxic compounds.

Examples include anti-tumor agents such as HERCEPTIN™ (trastuzumab), RITUXAN™ (rituximab), ZEVALIN™ (ibritumomab tiuxetan), LYMPHOCIDE™ (epratuzumab), GLEEVAC™ and BEXXAR™ (iodine 131 tositumomab).

Other anti-neoplastic agents/compounds that can be used in conjunction with the compounds of the present invention include anti-angiogenic compounds such as ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto).

Other anti-angiogenic compounds/agents that can be used in conjunction with the compounds of the present invention include Campath, IL-8, B-FGF, Tek antagonists, anti-TWEAK agents (e.g., specifically binding antibodies or antigen binding regions, or soluble TWEAK receptor antagonists, ADAM distintegrin domain to antagonize the binding of integrin to its ligands, specifically binding anti-eph receptor and/or anti-ephrin antibodies or antigen binding regions, and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Other anti-angiogenic/anti-tumor agents that can be used in conjunction with the compounds of the present invention include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA); ilomastat, (Arriva, USA,); emaxanib, (Pfizer, USA,); vatalanib, (Novartis, Switzerland); 2-methoxyestradiol, (EntreMed, USA); TLC ELL-12, (Elan, Ireland); anecortave acetate, (Alcon, USA); alpha-D 148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland); the ARGENT technology of Ariad, USA; YIGSR-Stealth, (Johnson & Johnson, USA); fibrinogen-E fragment, (BioActa, UK); the angiogenesis inhibitors of Trigen, UK; TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (WVAX, USA); Benefin, (Lane Labs, USA); Tz-93, (Tsumura, Japan); TAN-1120, (Takeda, Japan); FR-111142, (Fujisawa, Japan); platelet factor 4, (RepliGen, USA); vascular endothelial growth factor antagonist, (Borean, Denmark); bevacizumab (pINN), (Genentech, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProIX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrugs, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pIN), (Genaera, USA); RPI 4610, (Sima, USA); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA);vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

It is contemplated and therefore within the scope of the invention that the compounds of the present invention can be modified to target specific receptors or cancer cells or can be modified so that they can survive various in vivo environments. As examples, when X is a carboxylate functionality, X can be modified so that it is combined with dendrimers or other cyclic sugars to form carboxylate dendrimers or other sugars. It may be combined with steroids such as estrogen to form carboxylate steroids like carboxylate estrogen. X or other carboxylate functionalities on these compounds may be modified so that they contain folic acid. Those of skill in the art will recognize that there are other modifications that can be made to the compounds of the present invention so that they can target specific receptors, cells or provide stability to the compounds. It is contemplated that the compounds of the present invention can have modifications made that are covalent modifications, ionic modifications, modified so that they chelate to other compounds, or other undergo some other type of interaction that allows the compounds of the present invention to suit their use (such as hydrophobic or Van der Waals type interations).

In a further variation, the compounds of the present invention can be used against solid tumors, cell lines, and cell line tissue that demonstrate upregulated nucleotide excision repair and other upregulated resistance mechanisms.

The following references are incorporated by reference in their entireties:
1. Kelland, L., The resurgence of platinum-based cancer chemotherapy. *Nat. Rev. Cancer* 2007, 7, 573-584.
2. Rabik, C. A.; Dolan, M. E., Molecular mechanisms of resistance and toxicity associated with platinating agents. *Cancer Treat. Rev.* 2007, 33, 9-23.
3. Cosaert, J.; Quoix, E., Platinum drugs in the treatment of non-small-cell lung cancer. *Br. J. Cancer* 2002, 87, 825-833.
4. Wakelee, H.; Dubey, S.; Gandara, D., Optimal adjuvant therapy for non-small cell lung cancer—how to handle stage I disease. *Oncologist* 2007, 12, 331-337.
5. Soria, J. C.; Le Chevalier, T., Is cisplatin still the best platinum compound in non-small-cell lung cancer? *Ann. Oncol.* 2002, 13, 1515-1517.
6. Momekov, G.; Bakalova, A.; Karaivanova, M., Novel approaches towards development of non-classical platinum-based antineoplastic agents: design of platinum complexes characterized by an alternative DNA-binding pattern and/or tumor-targeted cytotoxicity. *Curr. Med. Chem.* 2005, 12, 2177-2191.
7. Guddneppanavar, R.; Bierbach, U., Adenine-n3 in the DNA minor groove—an emerging target for platinum containing anticancer pharmacophores. *Anticancer Agents Med. Chem.* 2007, 7, 125-138.
8. Martins, E. T.; Baruah, H.; Kramarczyk, J.; Saluta, G.; Day, C. S.; Kucera, G. L.; Bierbach, U., Design, synthesis, and biological activity of a novel non-cisplatin-type platinum-acridine pharmacophore. *J. Med. Chem.* 2001, 44, 4492-4496.
9. Baruah, H.; Rector, C. L.; Monnier, S. M.; Bierbach, U., Mechanism of action of non-cisplatin type DNA-targeted platinum anticancer agents: DNA interactions of novel acridinylthioureas and their platinum conjugates. *Biochem. Pharmacol.* 2002, 64, 191-200.
10. Barry, C. G.; Baruah, H.; Bierbach, U., Unprecedented monofunctional metalation of adenine nucleobase in guanine- and thymine-containing dinucleotide sequences by a cytotoxic platinum-acridine hybrid agent. *J. Am. Chem. Soc.* 2003, 125, 9629-9637.
11. Barry, C. G.; Day, C. S.; Bierbach, U., Duplex-promoted platination of adenine-N3 in the minor groove of DNA: challenging a longstanding bioinorganic paradigm. *J. Am. Chem. Soc.* 2005, 127, 1160-1169.
12. Baruah, H.; Wright, M. W.; Bierbach, U., Solution structural study of a DNA duplex containing the guanine-N7 adduct formed by a cytotoxic platinum-acridine hybrid agent. *Biochemistry* 2005, 44, 6059-6070.
13. Budiman, M. E.; Alexander, R. W.; Bierbach, U., Unique base-step recognition by a platinum-acridinylthiourea conjugate leads to a DNA damage profile complementary to that of the anticancer drug cisplatin. *Biochemistry* 2004, 43, 8560-8567.
14. Connors, T. A.; Cleare, M. J.; Harrap, K. R., Structure-Activity-Relationships of the Anti-Tumor Platinum Coordination-Complexes. *Cancer Treat. Rep.* 1979, 63, 1499-1502.
15. Hess, S. M.; Mounce, A. M.; Sequeira, R. C.; Augustus, T. M.; Ackley, M. C.; Bierbach, U., Platinum-acridinylthiourea conjugates show cell line-specific cytotoxic enhancement in H460 lung carcinoma cells compared to cisplatin. *Cancer Chemother. Pharmacol.* 2005, 56, 337-343.
16. Guddneppanavar, R.; Choudhury, J. R.; Kheradi, A. R.; Steen, B. D.; Saluta, G.; Kucera, G. L.; Day, C. S.; Bierbach, U., Effect of the diamine nonleaving group in platinum-acridinylthiourea conjugates on DNA damage and cytotoxicity. *J. Med. Chem.* 2007, 50, 2259-2263.
17. Guddneppanavar, R.; Saluta, G.; Kucera, G. L.; Bierbach, U., Synthesis, biological activity, and DNA-damage profile of platinum-threading intercalator conjugates designed to target adenine. *J. Med. Chem.* 2006, 49, 3204-3214.
18. Kukushkin, V. Y.; Pombeiro, A. J., Additions to metal-activated organonitriles. *Chem. Rev.* 2002, 102, 1771-1802.
19. Ackley, M. C.; Barry, C. G.; Mounce, A. M.; Farmer, M. C.; Springer, B. E.; Day, C. S.; Wright, M. W.; Berners-Price, S. J.; Hess, S. M.; Bierbach, U., Structure-activity relationships in platinum-acridinylthiourea conjugates: effect of the thiourea nonleaving group on drug stability, nucleobase affinity, and in vitro cytotoxicity. *J. Biol. Inorg. Chem.* 2004, 9, 453-461.
20. Guddneppanavar, R.; Wright, M. W.; Tomsey, A. K.; Bierbach, U., Guanine binding of a cytotoxic platinum-acridin-9-ylthiourea conjugate monitored by 1-D $^1$1-1 and 2-D [$^1$H-$^{15}$N] NMR spectroscopy: Hydrolysis is not the rate-determining step. *J. Inorg. Biochem.* 2006, 100, 972-979.
21. Gelasco, A.; Lippard, S. J., Anticancer activity of cisplatin and related complexes. In: *Topics in Biological Inorganic Chemistry, Vol 1*; Clarke, M. J., Sadler, P. J., Eds.; Springer: New York, 1999, pp 1-43.
22. Baruah, H.; Day, C. S.; Wright, M. W.; Bierbach, U., Metal-intercalator-mediated self-association and one-dimensional aggregation in the structure of the excised major DNA adduct of a platinum-acridine agent. *J. Am. Chem. Soc.* 2004, 126, 4492-4493.
23. Margiotta, N.; Habtemariam, A.; Sadler, P. J., Strong, rapid binding of a platinum complex to thymine and uracil under physiological conditions. Angew Chem. Int. Ed. Engl. 1997, 36, 1185-1187.
24. Manzotti, C.; Pratesi, G.; Menta, E.; Di Domenico, R.; Cavalletti, E.; Fiebig, H. H.; Kelland, L. R.; Farrell, N.; Polizzi, D.; Supino, R.; Pezzoni, G.; Zunino, F., BBR 3464: A novel triplatinum complex, exhibiting a preclinical profile of antitumor efficacy different from cisplatin. *Clin. Cancer Res.* 2000, 6, 2626-2634.
25. Hollis, L. S.; Amundsen, A. R.; Stern, E. W., Chemical and Biological Properties of a New Series of Cis-Diammineplatinum(II) Antitumor Agents Containing 3 Nitrogen Donors—Cis-[Pt(NH$_3$)$_2$(N-Donor)Cl]$^+$. *J. Med. Chem.* 1989, 32, 128-136.
26. Lovejoy, K. S.; Todd, R. C.; Zhang, S.; McCormick, M. S.; D'Aquino, J. A.; Reardon, J. T.; Sancar, A.; Giacomini, K. M.; Lippard, S. J., cis-Diammine(pyridine) chloroplatinum(II), a monofunctional platinum(II) antitumor agent: Uptake, structure, function, and prospects. *Proc. Natl. Acad. Sci. USA* 2008, 105, 8902-8907.
27. Gray, J.; Simon, G.; Bepler, G., Molecular predictors of chemotherapy response in non-small-cell lung cancer. *Expert Rev. Anticancer Ther.* 2007, 7, 545-549.
28. Weaver, D. A.; Crawford, E. L.; Warner, K. A.; Elkhairi, F.; Khuder, S. A.; Willey, J. C., ABCC5, ERCC2, XPA and XRCC1 transcript abundance levels correlate with cisplatin chemoresistance in non-small cell lung cancer cell lines. *Mol. Cancer.* 2005, 4, 18.
29. Fujii, T.; Toyooka, S.; Ichimura, K.; Fujiwara, Y.; Hotta, K.; Soh, J.; Suehisa, H.; Kobayashi, N.; Aoe, M.; Yoshino, T.; Kiura, K.; Date, H., ERCC1 protein expression predicts the response of cisplatin-based neoadjuvant chemotherapy in non-small-cell lung cancer. *Lung Cancer* 2008, 59, 377-384.
30. Soria, J. C., ERCC1-tailored chemotherapy in lung cancer: the first prospective randomized trial. *J. Clin. Oncol.* 2007, 25, 2648-2649.
31. Zamble, D. B.; Mu, D.; Reardon, J. T.; Sancar, A.; Lippard, S. J., Repair of cisplatin-DNA adducts by the mammalian excision nuclease. *Biochemistry* 1996, 35, 10004-10013.
32. Dip, R.; Camenisch, U.; Naegeli, H., Mechanisms of DNA damage recognition and strand discrimination in human nucleotide excision repair. *DNA Repair* 2004, 3, 1409-1423.
33. Poklar, N.; Pilch, D. S.; Lippard, S. J.; Redding, E. A.; Dunham, S. U.; Breslauer, K. J., Influence of cisplatin intrastrand crosslinking on the conformation, thermal stability, and energetics of a 20-mer DNA duplex. *Proc. Natl. Acad. Sci. USA* 1996, 93, 7606-7611.

It is contemplated and therefore within the scope of the present invention that any feature that is described above can be combined with any other feature that is described above. Moreover, it should be understood that the present invention contemplates minor modifications that can be made to the compounds, compositions and methods of the present invention. In any event, the present invention is defined by the below claims.

I claim:

1. A compound of Formula I:

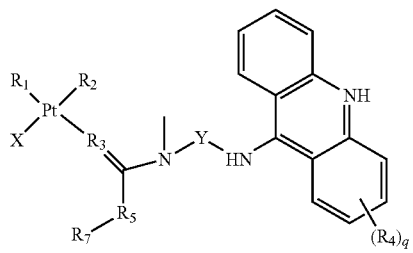

Formula I wherein X is halo, —OC(O)R$_9$, nitrate or sulfate:

R$_1$ and R$_2$ are amino groups or together with the platinum atom to which they are attached, R$_1$ and R$_2$ form the ring —NH$_2$—(CH$_2$)$_v$—NH$_2$— wherein v is 1, 2 or 3, or R$_1$ and R$_2$ together can be any of the following groups a-h, or R$_1$ and R$_2$ independently can be any of the following groups i-m;

a
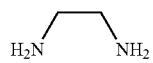

b
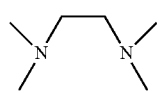

c
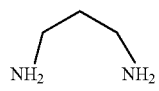

d
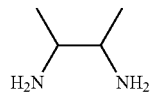

e
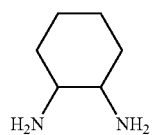

f
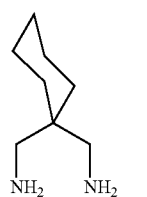

g
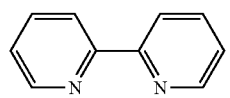

h
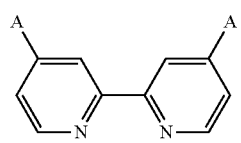

i

j
NH$_3$ k
NH$_2$R$_{13}$ l
NH(R$_{13}$)$_2$ m
N(R$_{13}$)$_3$ wherein A is H, —CH$_3$, —OCH$_3$, CF$_3$, or NO$_2$;

R$_{13}$ is independently C$_1$-C$_6$alkyl;

R$_3$ is —N(R$_6$)—, wherein R$_6$ is hydrogen or C$_1$-C$_6$alkyl;

R$_4$ is independently an amino, a nitro, —NHC(O)(R$_{10}$), —C(O)NHR$_{10}$, or halo;

R$_{10}$ is hydrogen, C$_{1-6}$ alkyl, phenyl, naphthyl, C$_{3-6}$ cycloalkyl, norhornyl, or adamantyl;

q is 0, 1, or 2;

R$_5$ is a direct bond, —NH— or C$_1$-C$_6$alkylene;

or R$_5$ and X together with the atoms to which they are attached form a 6- or 7-membered ring, wherein said 6- or 7-membered ring contains a linking group —C(O)O— or —OC(O)—;

R$_7$ is hydrogen, methyl, or —C(O)O—R$_8$; wherein

R$_8$ is hydrogen, C$_{1-6}$ alkyl, phenyl, naphthyl, C$_{3-6}$ cycloalkyl, norbornyl, or adamantyl, a natural or unnatural amino acid or a peptide;

R$_9$ is hydrogen, C$_{1-6}$ alkyl, phenyl, naphthyl, C$_{3-6}$ cycloalkyl, norbornyl, or adamantyl;

Y is C$_1$-C$_6$alkylene; and

Z is one or more counterions sufficient to balance the charge of the compound.

2. The compound of claim 1, wherein R$_6$ is hydrogen or methyl and R$_1$ and R$_2$ are amino groups or together with the platinum atom to which they are attached, R$_1$ and R$_2$ form the ring —NH$_2$—(CH$_2$)$_v$—NH$_2$— wherein v is 1, 2, or 3.

3. The compound of claim 2, wherein Y is —CH$_2$—.

4. The compound of claim 3, wherein R$_1$ and R$_2$ are amino groups or together with the platinum atom to which R$_1$ and R$_2$ are attached are —NH$_2$—CH$_2$—NH$_2$—.

5. The compound of claim 4, wherein the one or more counter ions of Z comprise NO$_3$.

6. The compound of claim 5, wherein R$_5$ is —NH— or —CH$_2$.

7. The compound of claim 6, wherein R$_6$ is hydrogen.

8. The compound of claim 1, wherein the compound is Example 1

Example 1

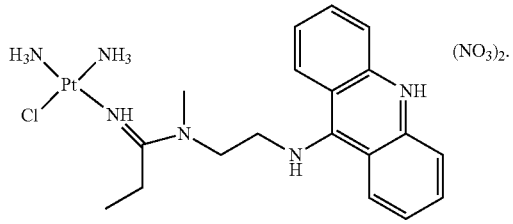

9. The compound of claim 1, wherein the compound is Example 2:

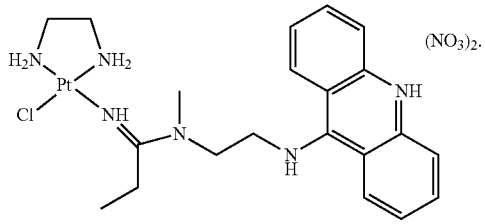

Example 2

10. A method of treating cancer comprising administering to a subject in need thereof an effective amount of the compound of Formula I:

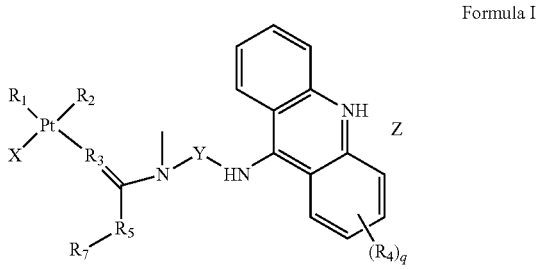

Formula I wherein X is halo, —OC(O)R$_9$, nitrate or sulfate;

R$_1$ and R$_2$ are amino groups or together with the platinum atom to which they are attached, R$_1$ and R$_2$ form the ring —NH$_2$—(CH$_2$)$_v$—NH$_2$— wherein v is 1, 2, or 3, or R$_1$ and R$_2$ together can be any of the following groups a-h or R$_1$ and R$_2$ independently can be any of the following groups i-m;

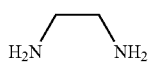
a

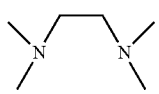
b

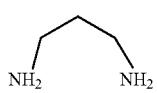
c

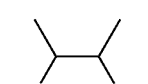
d

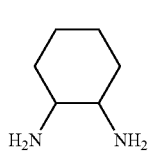
e

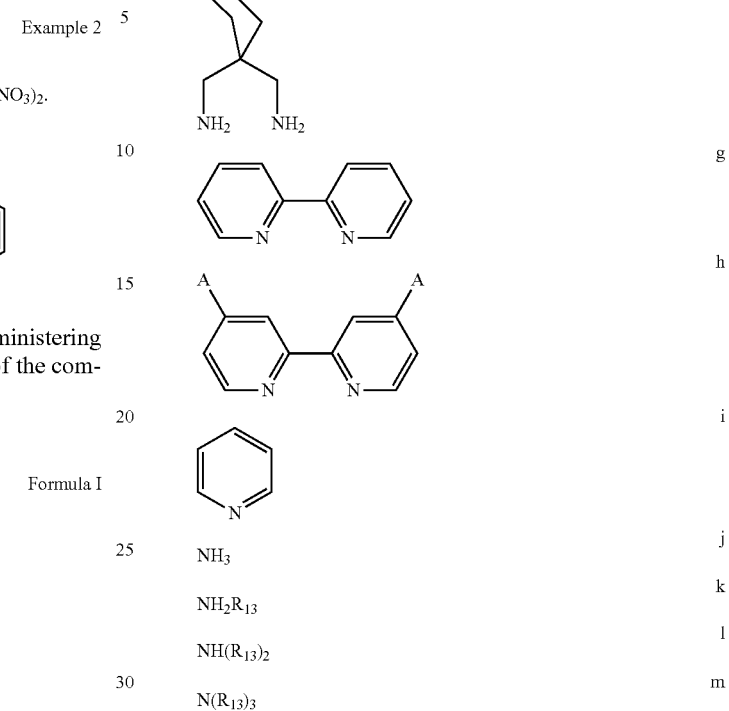

wherein A is H, —CH$_3$, —OCH$_3$, CF$_3$ or NO$_2$;

R$_{13}$ is independently C$_1$-C$_6$alkyl;

R$_3$ is —N(R$_6$)—; wherein R$_6$ is hydrogen or C$_1$-C$_6$alkyl;

R$_4$ is independently an amino, a nitro, —NHC(O)(R$_{10}$), —C(O)NHR$_{10}$, or halo;

R$_{10}$ is hydrogen, C$_{1-6}$ alkyl, phenyl, naphthyl, C$_{3-6}$ cycloalkyl, norbornyl, or adamantyl;

q is 0, 1, or 2;

R$_5$ is a direct bond, —NH— or C$_1$-C$_6$alkylene; or R$_5$ and X together with the atoms to which they are attached form a 6- or 7-membered ring, wherein said 6- or 7-membered ring contains a linking group —C(O)O— or —OC(O)—;

R$_7$ is hydrogen, methyl, or —C(O)O—R$_8$; wherein

R$_8$ is hydrogen, C$_{1-6}$ alkyl, phenyl, naphthyl, C$_{3-6}$ cycloalkyl, norbornyl, or adamantyl, a natural or unnatural amino acid or a peptide;

R$_9$ is hydrogen, C$_{1-6}$ alkyl, phenyl, naphthyl, C$_{3-6}$ cycloalkyl, norbornyl, or adamantyl;

Y is C$_1$-C$_6$alkylene; and

Z is one or more counterions sufficient to balance the charge of the compound.

11. The method of claim 10, wherein the cancer is selected from the group consisting of lung cancer, testicular cancers, ovarian carcinomas, head and neck cancers, leukemias and lymphomas.

12. The method of claim 11, wherein R$_6$ is hydrogen or methyl and R$_1$ and R$_2$ are amino groups or together with the platinum atom to which they are attached, R$_1$ and R$_2$ form the ring —NH$_2$—(CH$_2$)$_v$—NH$_2$— wherein v is 1, 2, or 3.

13. The method of claim 12, wherein Y is —CH$_2$—.

14. The method of claim 13, wherein R$_1$ and R$_2$ are amino groups or together with the platinum atom to which R$_1$ and R$_2$ are attached are —NH$_2$—CH$_2$—NH$_2$—.

15. The method of claim 14, wherein the one or more counter ions of Z comprise $NO_3$.

16. The method of claim 15, wherein $R_5$ is —NH— or —$CH_2$—.

17. The method of claim 16, wherein $R_6$ is hydrogen.

18. A pharmaceutical composition comprising the compound of Formula I:

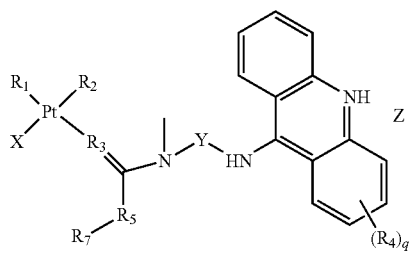

Formula I wherein X is halo, —OC(O)$R_9$, nitrate or sulfate;

$R_1$ and $R_2$ are amino groups or together with the platinum atom to which they are attached, $R_1$ and $R^2$ form the ring —$NH_2$—$(CH_2)_v$—$NH_2$— wherein v is 1, 2, or 3, or $R_1$ and $R_2$ together can be any of the following groups a-h or $R_1$ and $R_2$ independently can be any of the following groups i-m;

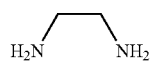 a

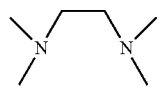 b

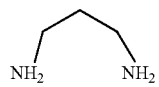 c

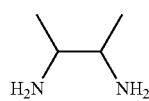 d

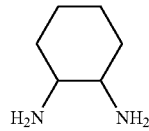 e

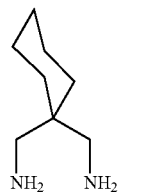 f

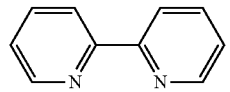 g

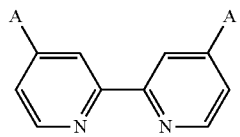 h

 i

NH$_3$ j

NH$_2$R$_{13}$ k

NH(R$_{13}$)$_2$ l

N(R$_{13}$)$_3$ m wherein A is H, —$CH_3$, —$OCH_3$, $CF_3$ or $NO_2$;

$R_{13}$ is independently $C_1$-$C_6$alkyl;

$R_3$ is —N($R_6$)—, wherein $R_6$ is hydrogen or $C_1$-$C_6$alkyl;

$R_4$ is independently an amino, a nitro, —NHC(O)($R_{10}$), —C(O)NHR$_{10}$, or halo;

$R_{10}$ is hydrogen, $C_{1-6}$ alkyl, phenyl, naphthyl, $C_{3-6}$ cycloalkyl, norbornyl, or adamantyl; q is 0, 1, or 2;

$R_5$ is a direct bond, —NH— or $C_1$-$C_6$alkylene; or $R_5$ and X together with the atoms to which they are attached form a 6- or 7-membered ring, wherein said 6- or 7-membered ring contains a linking group —C(O)O— or —OC(O)—;

$R_7$ is hydrogen, methyl, or —C(O)O—$R_8$; wherein $R_8$ is hydrogen, $C_{1-6}$ alkyl, phenyl, naphthyl, $C_{3-6}$ cycloalkyl, norbornyl, or adamantyl, a natural or unnatural amino acid or a peptide;

$R_9$ is hydrogen, $C_{1-6}$ alkyl, phenyl, naphthyl, $C_{3-6}$ cycloalkyl, norbornyl, or adamantyl;

Y is $C_1$-$C_6$alkylene; and

Z is one or more counterions sufficient to balance the charge of the compound; and a pharmaceutically acceptable diluent, carrier, or excipient.

19. The pharmaceutical composition of claim 18, wherein Y is —$CH_2$—, wherein $R_1$ and $R_2$ are amino groups or together with the platinum atom to which $R_1$ and $R_2$ are attached are —$NH_2$—$CH_2$—$NH_2$—, and wherein the one or more counter ions of Z comprise $NO_3$.

20. The pharmaceutical composition of claim 19, wherein $R_5$ is —NH— or —$CH_2$—, wherein $R_6$ is hydrogen or methyl and $R_1$ and $R_2$ are amino groups or together with the platinum atom to which they are attached, $R_1$ and $R_2$ form the ring —$NH_2$—$(CH_2)_v$—$NH_2$— wherein v is 1, 2, or 3.

21. The pharmaceutical composition of claim 18, further comprising one or more compounds selected from the group consisting of HERCEPTIN™ (trastuzumab), RITUXAN™ (rituximab), ZEVALIN™ (ibritumomab tiuxetan), LYMPHOCIDE™ (epratuzumab), GLEEVAC™, BEXXAR™ (iodine 131 tositumomab), ERBITUX™ (IMC-C225), KDR inhibitory agents, AVASTIN™, VEGF-TRAP™, ABX-EGF (panitumumab),IRESSA™ (gefitinib), TARCEVA™ (erlotinib), Campath, IL-8, B-FGF, Tek antagonists, anti-TWEAK agents, anti- PDGF-BB antagonists, SD-7784, cilengitide; pegaptanib octasodium; Alphastatin, M-PGA; ilomastat, emaxanib, vatalanib, 2-methoxyestradiol, TLC ELL- 12, anecortave acetate, alpha- D 148 Mab, CEP-7055, anti-Vn Mab, DAC:antiangiogenic, Angiocidin, KM-2550, SU-0879, CGP-79787, YIGSR-Stealth, fibrinogen-E fragment, TBC-1635; SC-236, ABT-567, Metastatin, maspin, ER-68203-00, Benefin, Tz-93, TAN-1120, FR-111142, platelet factor 4, vascular endothelial growth factor antagonist, bevacizumab (pINN), XL 784, XL 647, MAb, alpha5heat3 integrin, enzastaurin hydrochloride (USAN), CEP 7055, BC 1, VEGF antagonist, rBPI 21 and BPI-derived anti-angiogenic, PI 88, cilengitide (pINN), cetuximab (INN), AVE 8062, AS 1404, SG 292, Endostatin, ATN 161, ANGIOSTATIN, ZD 6474, ZD 6126, PPI 2458, AZD 9935, AZD 2171, vatalanib (pINN), pegaptanib (Pinn), xanthorrhizol, SPV5.2, SDX 103, PX 478, METASTATIN, troponin I, SU 6668, OXI 4503, o-guanidines, motuporamine C, CDP 791, atiprimod (pINN), E 7820, CYC 381, AE 941, urokinase plasminogen activator inhibitor, oglufanide (pINN), HIF-1alfa inhibitors, CEP 5214, BAY RES 2622; Angiocidin, A6, KR 31372, GW 2286, EHT 0101, CP 868596, CP 564959, CP 547632, compound 786034 from GlaxoSmithKline, KRN 633, anginex ABT 510, AAL 993, VEGI, tumor necrosis factor-alpha inhibitors, SU 11248, ABT 518, YH 16, S-3APG, KDR, GFB 116, CS 706, combretastatin A4 prodrugs, chondroitinase AC, BAY RES 2690, AGM 1470, AG 13925, Tetrathiomolybdate, GCS 100, CV 247, CKD 732, irsogladine (INN), RG 13577, WX 360, squalamine (pIN), RPI 4610, heparanase inhibitors, KL 3106, Honokiol, ZK CDK, ZK Angio, ZK 229561, XMP 300, VGA 1102, Vasostatin, Flk-I, TZ 93, TumStatin, truncated soluble FLT 1 Tie-2 ligands and thrombospondin 1 inhibitor.

22. A method of making a compound of Formula X:

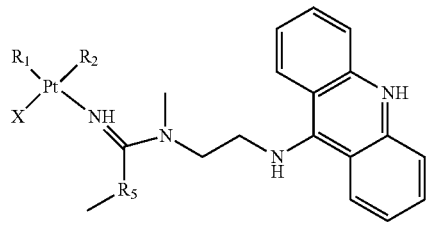

Formula X wherein X is a halo group;

$R_1$ and $R_2$ are amino groups or together with the platinum atom to which they are attached, $R_1$ and $R_7$ form the ring —$NH_2$—$(CH_2)_v$—$NH_2$— wherein v is 1, 2, or 3, or $R_1$ and $R_2$ together can be any of the following groups a-h, or $R_1$ and $R_2$ independently can be an of the following groups i-m:

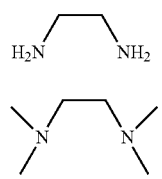  a b

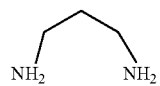  c

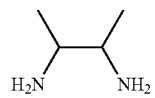  d

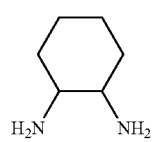  e

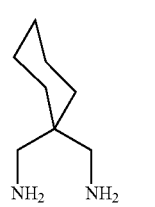  f

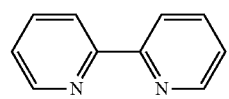  g

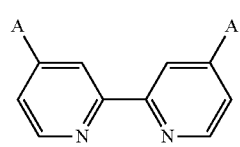  h

  i $NH_3$  j $NH_2R_{13}$  k $NH(R_{13})_2$  l $N(R_{13})_3$  m wherein A is H, —$CH_3$, —$OCH_3$, $CF_3$ or $NO_2$;

$R_{13}$ is independently $C_1$-$C_6$alkyl;

$R_5$ is a direct bond, —NH— or $C_1$-$C_6$alkylene; and

Z is one or more counterions sufficient to balance the charge of the compound comprising reacting a compound of Formula IV

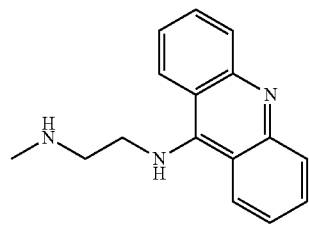

Formula IV with a compound of formula V

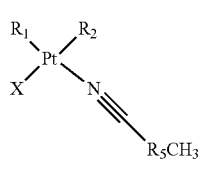

Formula V wherein all of the variables are defined as above.

23. The method of claim 10, wherein the cancer is non-small cell lung, leukemia, ovarian, pancreatic, breast, gastrointestinal, prostate, melanoma, acute leukemia, multiple myeloma, lymphocytic lymphomas, lymphoblastic leukemia, follicular lymphoma, or lymphoid malignancies of T-cell or B-cell origin.

24. The method of claim 10, wherein the cancer is non-small cell lung, leukemia, ovarian, breast, or pancreatic.

25. The method of claim 10, wherein the cancer is non-small cell lung or leukemia.

\* \* \* \* \*